United States Patent
Nolan et al.

(10) Patent No.: US 6,833,245 B2
(45) Date of Patent: Dec. 21, 2004

(54) METHODS FOR SCREENING FOR TRANSDOMINANT EFFECTOR PEPTIDES AND RNA MOLECULES

(75) Inventors: Garry P. Nolan, San Francisco, CA (US); S. Michael Rothenberg, Boston, MA (US)

(73) Assignees: Rigel Pharmaceuticals, Inc., South San Francisco, CA (US); The Board of Trustees of the Leland Stanford Junior University, Palo Alto, CA (US)

(*) Notice: Subject to any disclaimer, the term of this patent is extended or adjusted under 35 U.S.C. 154(b) by 133 days.

(21) Appl. No.: 10/096,550

(22) Filed: Mar. 12, 2002

(65) Prior Publication Data

US 2003/0170641 A1 Sep. 11, 2003

Related U.S. Application Data

(63) Continuation of application No. 08/787,738, filed on Jan. 23, 1997, now Pat. No. 6,455,247, which is a continuation-in-part of application No. 08/589,109, filed on Jan. 23, 1996, now Pat. No. 6,365,344.

(51) Int. Cl.[7] .................... C12Q 1/68; C12N 15/11; C12N 15/64
(52) U.S. Cl. .............. 435/6; 435/69.7; 435/320.1; 435/456; 536/23.4
(58) Field of Search .................. 435/6, 69.7, 320.1, 435/456; 536/23.4

(56) References Cited

U.S. PATENT DOCUMENTS

| | | |
|---|---|---|
| 4,618,578 A | 10/1986 | Burke et al. |
| 4,980,281 A | 12/1990 | Housey et al. |
| 5,217,889 A | 6/1993 | Roninson et al. |
| 5,223,408 A | 6/1993 | Goeddel et al. |
| 5,266,464 A | 11/1993 | Housey et al. |
| 5,283,173 A | 2/1994 | Fields et al. |
| 5,639,595 A | 6/1997 | Mirabelli et al. |
| 5,650,489 A | 7/1997 | Lam et al. |
| 5,688,655 A | 11/1997 | Housey et al. |
| 5,698,396 A | 12/1997 | Pfreundschuh |
| 5,723,287 A | 3/1998 | Russell et al. |
| 5,723,323 A | 3/1998 | Kauffman et al. |
| 5,747,334 A | 5/1998 | Kay et al. |
| 5,763,192 A | 6/1998 | Kauffman et al. |
| 5,770,434 A | 6/1998 | Huse |
| 5,814,476 A | 9/1998 | Kauffman et al. |
| 5,817,483 A | 10/1998 | Kauffman et al. |
| 5,824,514 A | 10/1998 | Kauffman et al. |
| 5,840,479 A | 11/1998 | Little et al. |
| 5,877,007 A | 3/1999 | Housey et al. |
| 5,935,823 A | 8/1999 | Fowlkes et al. |
| 5,955,275 A | 9/1999 | Kamb et al. |
| 6,153,380 A | 11/2000 | Nolan et al. |
| 6,194,544 B1 | 2/2001 | Huffman et al. |
| 6,365,344 B1 * | 4/2002 | Nolan et al. .............. 435/6 |
| 6,455,247 B1 * | 9/2002 | Nolan et al. .............. 435/6 |
| 2001/0053523 A1 | 12/2001 | Jenson et al. |

FOREIGN PATENT DOCUMENTS

| | | |
|---|---|---|
| EP | 0 334 301 B1 | 9/1989 |
| EP | 0440146 A2 | 9/1989 |
| EP | 0 383 620 | 8/1990 |
| EP | 0 557 897 A1 | 9/1993 |
| WO | WO 86/05803 | 10/1986 |
| WO | WO 90/02809 | 3/1990 |
| WO | WO 91/17266 | 11/1991 |
| WO | WO 91/19818 | 12/1991 |
| WO | WO 92/05266 | 4/1992 |
| WO | WO 92/07071 | 4/1992 |
| WO | WO 93/03143 | 2/1993 |
| WO | WO 93/08278 | 4/1993 |
| WO | WO 93/23569 | 11/1993 |
| WO | WO 94/06920 | 3/1994 |
| WO | WO 94/18219 | 8/1994 |
| WO | WO 94/19478 | 9/1994 |
| WO | WO 94/20608 | 9/1994 |
| WO | WO 94/29469 | 12/1994 |
| WO | WO 95/04824 | 2/1995 |
| WO | WO 95/11998 | 5/1995 |
| WO | WO 95/16054 | 6/1995 |
| WO | WO 96/23899 | 8/1996 |
| WO | WO 96/38553 | 12/1996 |
| WO | WO 96/40987 | 12/1996 |
| WO | WO 00/05406 | 2/2000 |

OTHER PUBLICATIONS

Abbas et al., "Cytokines", (1994), Cellular and Molecular Immunology, Ch. 11.

Berkhout et al., "In vivo selection of randomly mutated retroviral genomes", (1993), Nucleic. Acids. Res., 21(22): 5020–5024.

Bock et al., "Selection of single–stranded DNA molecules that bind and inhibit human thrombin", Nature, (1992), 355(6360): 564–6.

Cadwell et al., "Randomization of Genes by PCR Mutagenesis," Abstract excerpted from: PCR Methods and Applications, 2(1): 28–33 (1992) (Abstract No. XP 00203396).

Caldwell et al., "Molecular determinants of bioactivity of t eSaccharomyces cerevisiae lipopeptide mating pheromone", (1994), J. Biol. Chem., 31: 19817–23.

Caldecott et al., "An Interaction between the Mammalian DNA Repair Protein XRCC1 and DNA Ligase III", (1994), Mol. Cell. Biol., 14(1): 68–76.

Choo et al., "Selection of DNA binding sites for zinc fingers using rationally randomized DNA reveals coded interactions", Proc. Natl. Acad. Sci. USA, (1994), 8:91(23): 11168–72.

(List continued on next page.)

Primary Examiner—John S. Brusca
(74) Attorney, Agent, or Firm—James S. Keddie; Carol L. Francis; James J. Diehl

(57) ABSTRACT

Methods and compositions for screening for transdominant effector peptides and RNA molecules selected inside living cells from randomized pools are provided.

15 Claims, 4 Drawing Sheets

OTHER PUBLICATIONS

Cull et al., "Screening for receptor ligands using large libraries of peptides linked to the C terminus of the lac repressor", (1992), Proc. Nat. Acad. Sci., 89: 1865–69.

Cwirla, S. et al., "Peptides on Phage: A vast library of peptides for identifying ligands" Proc. Natl. Acad. Sci. USA, vol. 87, Aug. 1990, pp. 6378–6382.

D'Andrea et al., "A mutation of the common receptor subunit for interleukin–3 (IL–3), granulocyte–macrophage colony–stimulating factor, and IL–5 that leads to ligand independence and tumorigenicity", (1994), Blood, 83(10): 2802–8.

D'Andrea et al., "Extracellular truncations of h beta c, the common signaling subunit for interleukin–3 (IL–3), granulocyte–macrophage colony–stimulating factor (GM–CSF), and IL–5, lead to ligand–independent activation", (1996), Blood, 87(7): 2641–8.

Deng et al., "Basis for selection of improved carbohydrate–binding single–chain antibodies from synthetic gene libraries", (1995), Proc. Natl. Acad. Sci., 92: 4992–4996.

Denmark patent application No. 0629/95, "A Method for Identification of Biologically Active Peptides and Nucleid Acids", (1995).

Drucker et al., "Generation of a large library of point mutations in polyoma middle T antigen", (1991), Nuc. Acids Res., 19(24): 6855–6861.

Dube et al., "Selection of new biologically active molecules from random nucleotide sequences." Gene vol. 137, Aug. 1993, pp. 41–47.

Duenas, M. et al., "Clonal Selection and Amplification of Phage Displayed Antibodies by Linking Antigen Recognition and Phage and Phage Replication", BIO/TECHNOLOGY, vol. 12, Oct. 1994, pp. 999–1002.

Fong et al., "Scanning Whole Cells with Phage–Display Libraries: Identification of Peptide Ligands that Modulate Cell Function", (1994), Drug Development Research, 33: 64–70.

Furka, A. et al., "General method for rapid synthesis of multi–component peptide mixtures", Int. J. Peptide Protein Res., 37, 1991 pp. 487–493.

Gavin et al., "Major histocampatibility complex class I allele–specific peptide libraries: identification of peptides that mimic an H–Y T cell epitope", (1994), Eur. J. Immunol., 24: 2124–2133.

Gissel, B. et al., "Identification of Avidin and Streptavidin Binding Motifs Among Peptides Selected from a Synthetic Peptide Library Consisting solely of D–Amino Acids", Journal of Peptide Science, vol. 1, 1995, pp. 217–226.

Groger et al., "Directional antisense and sense cDNA cloning usin gEpstein–Barr virus episomal expression vectors", (1989), Gene, 81(2): 285–94.

Gudkov, A.V. et al., "Isolation of genetic suppressor elements, inducing resistance to topoisomerase II–interactive cytotoxic drugs, from human topoisomerase II cDNA", (1993), Proc. Natl. Acad. Sci., 90(8): 3231–3235, Proc. Nat. Acad. Sci. USA., 90(8): 3231–3235.

Gudkov et al., "Cloning mammalian genes by expression selection of genetic suppressor elements: Association of kinesin with drug resistance and cell immortalization", (1994), Proc. Natl. Acad. Sci., 91: 3744–3748.

Houghten, R. et al., "Generation and use of synthetic peptide combinatorial libraries for basic research and drug discovery" Nature, vol. 354, Nov. 7, 1991, pp. 84–86.

Hupp et al., "Small Peptides Activate the Latent Sequence–Specific DNA Binding Function of p53", (1995), Cell, 83: 237–245.

Ito et al., "A general method for introducing a series of mutations into cloned DNA using the epolymerase chain reaction", (1991), Gene, 102: 67–70.

Jellis et al., "Defining critical residues in the epitope for a HIV–neutralizing monoclonal antibody using phage display and peptide array technologies", (1993), Gene, 137: 63–68.

Jenkins et al., "Activating point mutations in the common beta subunit of the human GM–CSF, IL–3 and IL–5 receptors suggest the involvement of beta subunit dimerization and cell type–specific molecules in signaling", (1995), EMBO J., 14(17): 4276–87.

Karttunen et al., Detection of rare antigen–presenting cells by the lacZ T–cell activation assay suggests an expression cloning strategy for T–cell antigens. Proc. Natl. Acad. Sci. USA, vol. 89, 1992, pp.

Kauffman, S. et al., "Vectors Used for Expression in Mammalian Cells", (1990), Meth. Enzymol., 185: 487–511.

Kauffman, S. et al., "The NK Model of Rugged Fitness Landscapes And Its Application to Maturation of the Immune Response" J. Theor. Biol., vol. 141(2), 1989, pp. 211–245.

Kauffman, S. et al., "Toward a General Theory of Adaptive Walks on Rugged Landscapes", J. Theor. Biol. vol. 128(1), 1987, pp. 11–45.

Kim et al., "Diversified sequences of peptide epitope for same–RNA recognition", (1993), Proc. Natl. Acad. Sci., 90: 10046–10050.

Kitamura, T. et al., "Efficient Screening of Retroviral cDNA Expression Libraries", (1995), PNAS, USA, 92: 9146–9150.

Labean et al., "Design of synthetic gene libraries encoding random sepuence proteins with desired ensemble characteristics", (1993), Protein Science, 2: 1249–1254.

Lam, K. et al., "A new type of synthetic peptide library for identifying ligand–binding activity", Nature vol. 354, Nov. 7, 1991, pp. 82–84.

Long, E. et al., "Invariant Chain Prevents the HLA–DR Restricted Presentation of a Cytosolic Peptide", The Journal of Immunology, 153, 1994, pp. 1487–1494.

Lund, A. et al., "Increased cloning efficiency by temperature cycle ligation", Nucleic Acids Research, vol. 24, No. 4, 1996, pp 800–801.

Luzzago et al., "Mimicking of discontinuous epitopes by phage–displayed peptides. I. Epitope mapping of human H ferritin using a phage library of constrained peptides", (1993), Gene, 128: 51–57.

Malnati, M. et al., "Processing pathways for presentation of cytosolic antigen to MHC class II–restricted T cells", Nature vol. 357, Jun. 25, 1992, pp. 702–704.

Mann et al., "Construction of a retrovirus packaging mutant and its use to produce helper–free defective retrovirus", (1983), Cell, 33(1): 153–9.

Martin et al., "The affinity–selection of a minbody polypeptide inhibitor of human interleukin–6", (1994), EMBO J., 13(22): 5303–5309.

Miller, A.D. et al., "Improved Retroviral Vectors for Gene Transfer and Expression", BioTechniques, vol. 7, No. 9, 1989, pp. 980–990.

Murphy, A. et al., "pλzd39: A new type of cDNA expression vector for low background, high efficiency directional cloning", Nucleic Acids Research, vol. 19, No. 12, (1991), pp. 3403–3408.

Murphy et al., "Cloning vectors for expression of cDNA libraries in mammalian cells", (1987), Proc. Natl. Acad. Sci., 84: 8277–8281.

Nilsson et al., "Fusion proteins in biotechnology and structural biology", (1992), Curr. Opin. Struc. Biol., 2: 569:575.

Palzkill et al., "Selection of Functional Signal Peptide Cleavage Sites from a Library of Random Sequences", (1994), J. Bacteriology, 176: 563–568.

Pan et al., "Isolation of virus–neutralizing RNAs from a large pool of random sequences", (1995), Proc. Natl. Acad. Sci. USA, 92(25): 11509–13.

Pear et al., "Production of high–titer helper free retroviruses by transclent trasfection", (1993), PNAS, 90: 8392–8396.

Raynor et al., "A Simple and Efficient Procedure for Generating Stable Expression Libraries by cDNA Cloning in a Retroviral Vector", (1994), Mol. Cell. Biol., 14(2): 880–887.

Roninson et al., "Genetic Suppressor Elements: New Tools for Molecular Oncology–Thirteenth Cornelius P. Rhods Memorial Award Lecture", (1995), Cancer Res., 55: 4023–4028.

Schumacher, T et al., "Synthetic peptide libraries in the determination of T cell epitopes and peptide binding specificity of class I molecules", Eur. J. Immunol. (Germany), vol. 22 (6), Jun. 1992, pp. 1405–1412.

Scott, J., "Discovering peptide ligands using epitope libraries", TIBS 17, (1992), pp. 241–245.

Scott et al., "Random Peptide Libraries, (1994), Current Opinion in Biotechnology", 5: 40–48.

Seed, B. et al., "Molecular cloning of the CD2 antigen, the T–cell erythrocyte receptor, by a rapid immunoselection procedure", Proc. Natl. Acad. Sci. USA, vol. 84, May 1987, pp. 3365–3369.

Stuhlmann et al., "Introduction of a selectable gene into diffeent animal tissue by a retrovirus recombinant vector", (1984), Proc. Natl. Acad. Sci., 81: 7151–7155.

Van Den Hazel et al., "Random Substitution of Large Parts of the Propeptide of Yeast Proteinase A", (1995), J. Biol. Chem., 270(15): 8602–8609.

Virnekes et al., "Trinucleotide phosphoramidetes: ideal reagents for the synthesis of mixed oligonucleotides for random mutogenesis", (1994), Nucleic Acids Res., 22(25): 5600–5607.

Whitehead et al., "Expression cloning of oncogenes by retroviral transfer of cDNA libraries", (1995), Mol. Cell. Biol., 15(2): 704–10.

Whiteway et al., "Dominant negative selection of heterologous genes: Isolation of *Candida albicans* genes that interfere with *Saccharomyces cerevisiae* mating factor–induced cell cycle arrest", (1992), Proc. Natl. Acad. Sci., 89: 9410–9414.

Winnacker et al., "From genes to clones: Introduction to Gene Technology", (1987), VCH, 260–270.

Winnacker et al., "From genes to clones: Introduction to Gene Technology", (1987), VCH, 359.

Winnacker et al., "From genes to clones: Introduction to Gene Technology", (1987), VCH, 363–370.

Winnacker et al., "From genes to clones: Introduction to Gene Technology", (1987), VCH, 373–374.

Wong et al., "High–Efficiency Identification of Genes by Functional Analysi from a Retroviral cDNA Expression Library", (1994), J. Virology, 68(9): 5523–5531.

Yang et al., "Protein–peptide interactions analyzed with the yeast two–hybrid system", (1995), Nuc. Acids Res., 23(7): 1152–6.

Youssoufian et al., "Localization of Fanconl anemia C protein to the cytoplasm of mammalian cells," (1994), Proc. Natl. Acad. Sci., 91: 7975–7979.

Roitt et al., "Kurzes Lehrbuch der Immunologie", 2, Auflage, P. 86, (1991) Statement of Significance: this references discusses antigen presentation to T cells.

Rompp et al., Bd. 5 P1–S, (1995), Georg Thieme Verlag Stuttgart, (In German) Statement of Significance: this reference provides a definition of "Polymerase Chain Reaction", p. 3543.

Stryer et al., Biochemie, Heidelberg, Berlin: Spektrum–Verlag, (1994), pp. 53–57 (In German)(published in America in Stryer, (1988), L. Biochemistry $3^{rd}$ Ed., New York: W.H. Freeman and Company, pp. 50–55) An English version of this reference is provided.

Stryer et al., Biochemie, Heidelberg, Berlin: Spektrum–Verlag, (1994), pp. 124–126 (In German)(published in American in Stryer, (1988), L. Biochemistry $3^{rd}$ Ed., New York: W.H. Freeman and Company, pp. 120–123) An English version of this reference is provided.

Stryer et al., Biochemie, Heidelberg, Berlin: Spektrum–Verlag, (1994), pp. 807–808(In German)(published in America in Stryer, (1988), L. Biochemistry $3^{rd}$ Ed., New York: W.H. Freeman and Company, pp. 773–775) An English version of this reference is provided.

ATCC catalog internet printout regarding cell line HB–101, published to the world wide website of the ATCC at *www.atcc.org*, USA, in 2001.

* cited by examiner

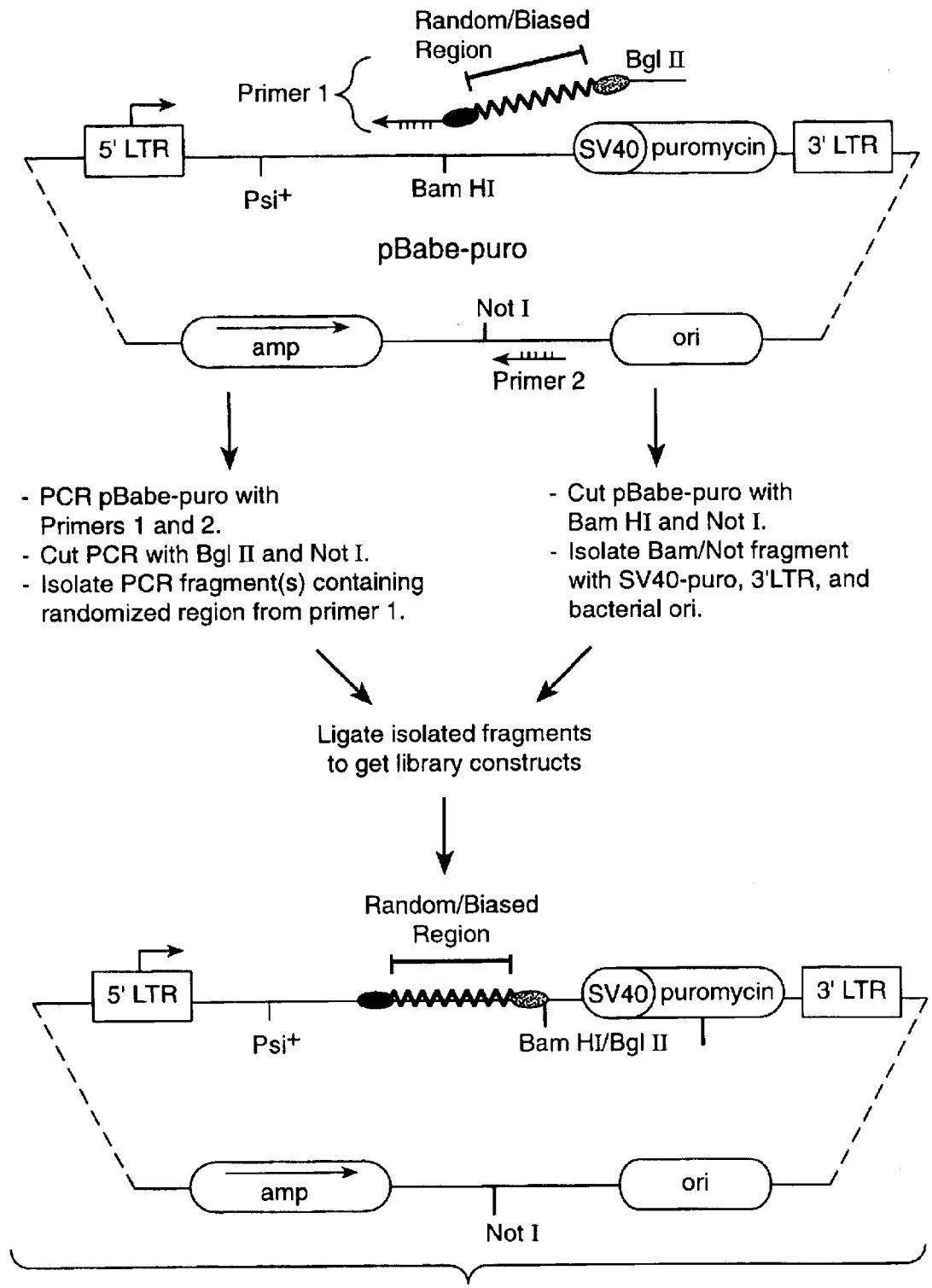
FIG._1

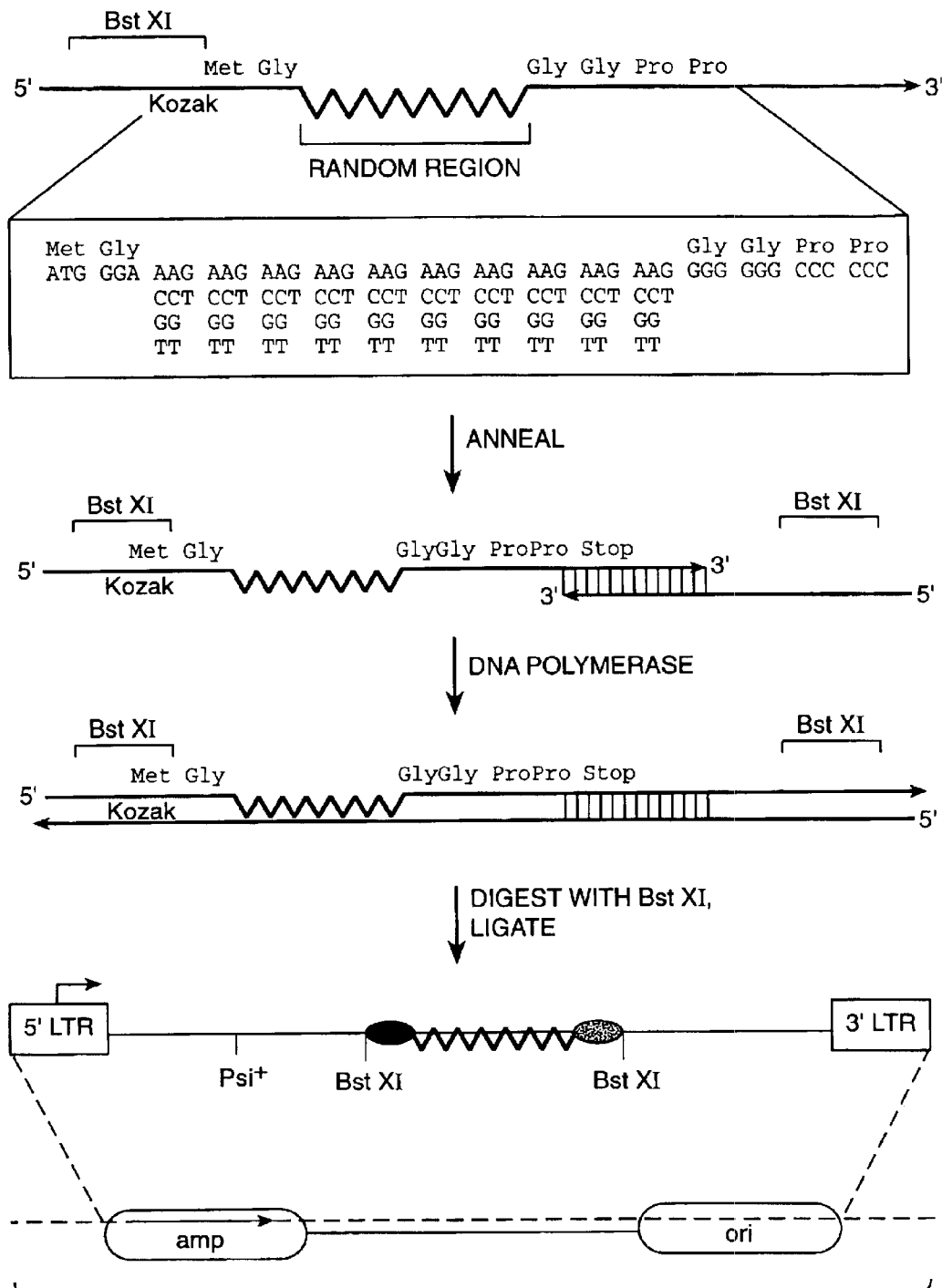
FIG._2

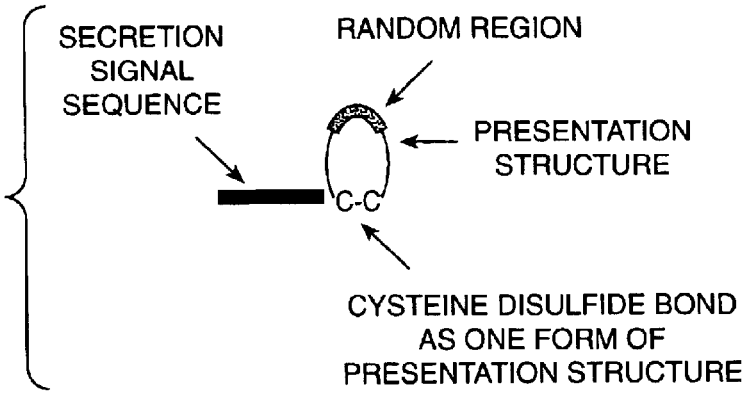
FIG._3A
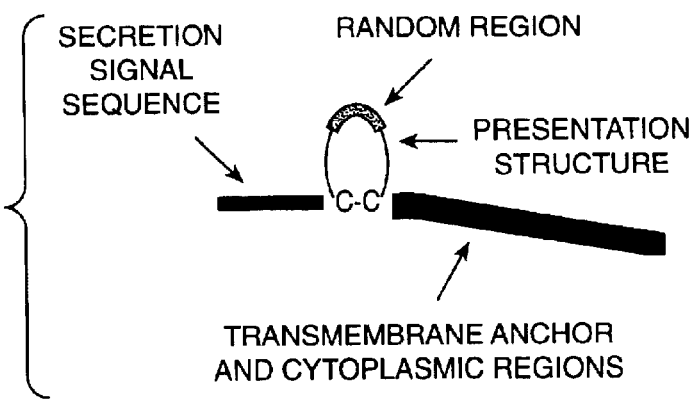
FIG._3B
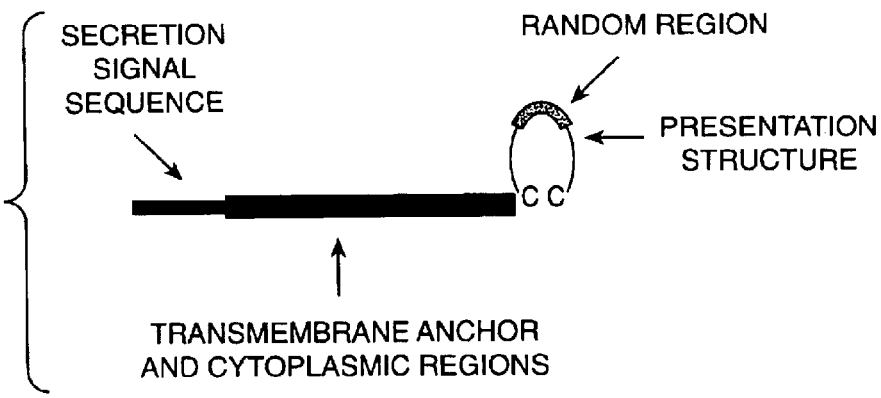
FIG._3C

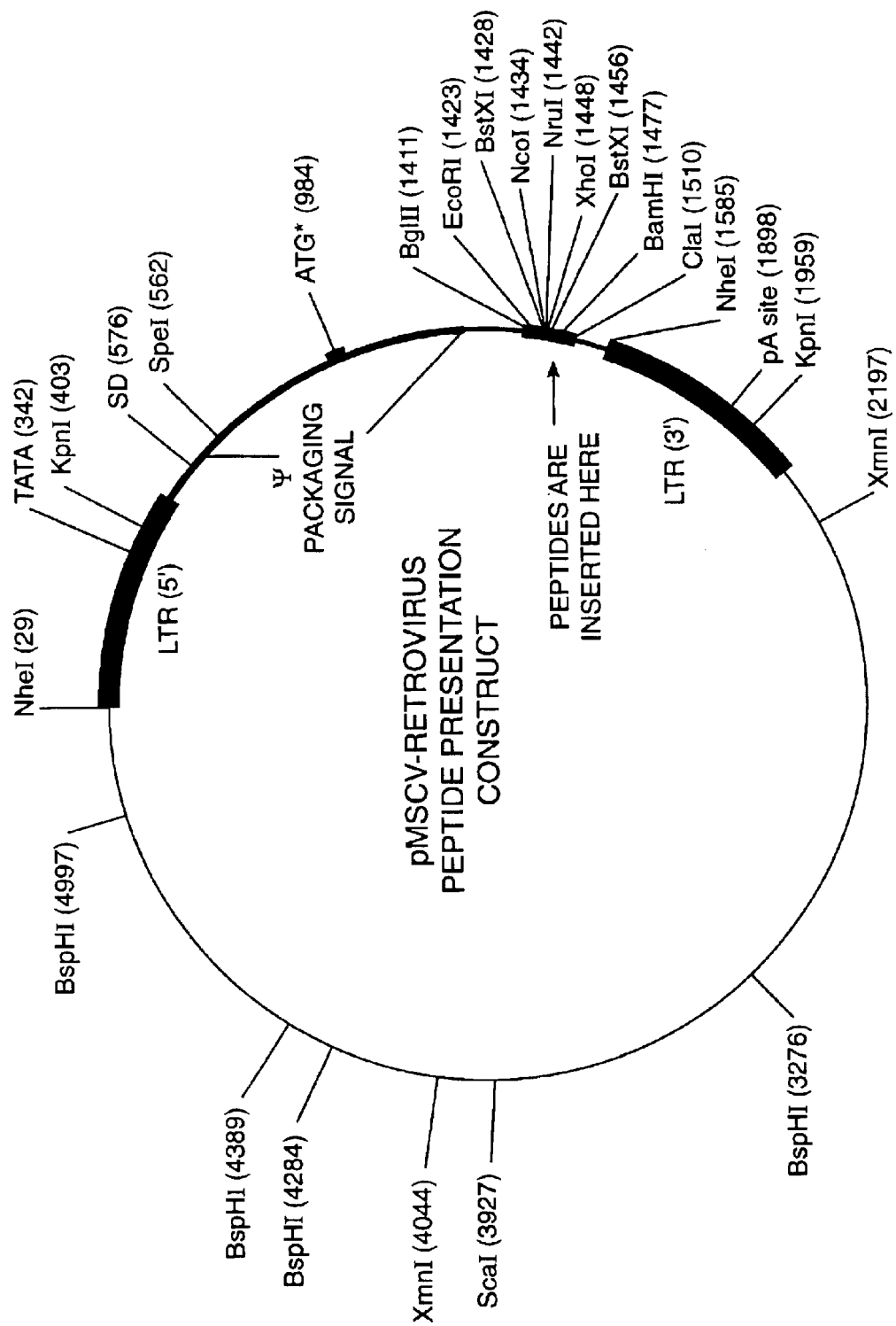
FIG._4

SEQUENCE LISTING

```
<160> NUMBER OF SEQ ID NOS: 97

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: random
      sequence.
<220> FEATURE:
<221> NAME/KEY: misc_feature
<222> LOCATION: (7)..(35)
<223> OTHER INFORMATION: The n(s) at positions
      7,8,10,11,13,14,16,17,19,20,22,23,25,26,28,29,31,3
      2,34,35 can be any nucleic acid.

<400> SEQUENCE: 1
atgggannkn nknnknnknn knnknnknnk nnknnkgggg ggcccccc                    48

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: random
      sequence.
<220> FEATURE:
<221> NAME/KEY: VARIANT
<222> LOCATION: (3)..(12)
<223> OTHER INFORMATION: The Xaa(s) at positions 3-12 can be any amino
      acid.

<400> SEQUENCE: 2

Met Gly Xaa Xaa Xaa Xaa Xaa Xaa Xaa Xaa Xaa Xaa Gly Gly Pro Pro
 1               5                  10                  15

<210> SEQ ID NO 3
<211> LENGTH: 4
<212> TYPE: PRT
<213> ORGANISM: Artificial Sequence
```

```
<220> FEATURE:
<223> OTHER INFORMATION: Description of Artificial Sequence: random
      sequence.

<400> SEQUENCE: 3

Gly Gly Pro Pro
 1

<210> SEQ ID NO 4
<211> LENGTH: 61
<212> TYPE: PRT
<213> ORGANISM: Artificial Sequence
<220> FEATURE:
<223> OTHER INFORMATION: Description of Artificial Sequence: coiled-coil
      structure.

<400> SEQUENCE: 4

Met Gly Cys Ala Ala Leu Glu Ser Glu Val Ser Ala Leu Glu Ser Glu
 1               5                  10                  15

Val Ala Ser Leu Glu Ser Glu Val Ala Ala Leu Gly Arg Gly Asp Met
                20                  25                  30

Pro Leu Ala Ala Val Lys Ser Lys Leu Ser Ala Val Lys Ser Lys Leu
            35                  40                  45

Ala Ser Val Lys Ser Lys Leu Ala Ala Cys Gly Pro Pro
        50                  55                  60

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: loop
      structure.

<400> SEQUENCE: 5

Gly Arg Gly Asp Met Pro
 1               5

<210> SEQ ID NO 6
<211> LENGTH: 69
<212> TYPE: PRT
<213> ORGANISM: Artificial Sequence
<220> FEATURE:
<223> OTHER INFORMATION: Description of Artificial Sequence: minibody
      presentation structure.

<400> SEQUENCE: 6

Met Gly Arg Asn Ser Gln Ala Thr Ser Gly Phe Thr Phe Ser His Phe
 1               5                  10                  15

Tyr Met Glu Trp Val Arg Gly Gly Glu Tyr Ile Ala Ala Ser Arg His
                20                  25                  30

Lys His Asn Lys Tyr Thr Thr Glu Tyr Ser Ala Ser Val Lys Gly Arg
            35                  40                  45

Tyr Ile Val Ser Arg Asp Thr Ser Gln Ser Ile Leu Tyr Leu Gln Lys
        50                  55                  60

Lys Lys Gly Pro Pro
 65

<210> SEQ ID NO 7
<211> LENGTH: 7
<212> TYPE: PRT
<213> ORGANISM: Simian virus 40

<400> SEQUENCE: 7
```

```
Pro Lys Lys Lys Arg Lys Val
 1               5

<210> SEQ ID NO 8
<211> LENGTH: 6
<212> TYPE: PRT
<213> ORGANISM: Homo sapiens
<220> FEATURE:

<400> SEQUENCE: 8

Ala Arg Arg Arg Arg Pro
 1               5

<210> SEQ ID NO 9
<211> LENGTH: 10
<212> TYPE: PRT
<213> ORGANISM: Mus musculus

<400> SEQUENCE: 9

Glu Glu Val Gln Arg Lys Arg Gln Lys Leu
 1               5                  10

<210> SEQ ID NO 10
<211> LENGTH: 9
<212> TYPE: PRT
<213> ORGANISM: Mus musculus

<400> SEQUENCE: 10

Glu Glu Lys Arg Lys Arg Thr Tyr Glu
 1               5

<210> SEQ ID NO 11
<211> LENGTH: 20
<212> TYPE: PRT
<213> ORGANISM: Xenopus laevis

<400> SEQUENCE: 11

Ala Val Lys Arg Pro Ala Ala Thr Lys Lys Ala Gly Gln Ala Lys Lys
 1               5                  10                  15

Lys Lys Leu Asp
            20

<210> SEQ ID NO 12
<211> LENGTH: 31
<212> TYPE: PRT
<213> ORGANISM: Mus musculus

<400> SEQUENCE: 12

Met Ala Ser Pro Leu Thr Arg Phe Leu Ser Leu Asn Leu Leu Leu Leu
 1               5                  10                  15

Gly Glu Ser Ile Leu Gly Ser Gly Glu Ala Lys Pro Gln Ala Pro
            20                  25                  30

<210> SEQ ID NO 13
<211> LENGTH: 21
<212> TYPE: PRT
<213> ORGANISM: Homo sapiens

<400> SEQUENCE: 13

Met Ser Ser Phe Gly Tyr Arg Thr Leu Thr Val Ala Leu Phe Thr Leu
 1               5                  10                  15

Ile Cys Cys Pro Gly
            20
```

<210> SEQ ID NO 14
<211> LENGTH: 51
<212> TYPE: PRT
<213> ORGANISM: Mus musculus

<400> SEQUENCE: 14

Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
             20                  25                  30

Ile Cys Val Ala Leu Leu Leu Ser Leu Ile Ile Thr Leu Ile Cys Tyr
         35                  40                  45

His Ser Arg
     50

<210> SEQ ID NO 15
<211> LENGTH: 33
<212> TYPE: PRT
<213> ORGANISM: Homo sapiens

<400> SEQUENCE: 15

Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
             20                  25                  30
Arg

<210> SEQ ID NO 16
<211> LENGTH: 37
<212> TYPE: PRT
<213> ORGANISM: Rattus sp.

<400> SEQUENCE: 16

Pro Asn Lys Gly Ser Gly Thr Thr Ser Gly Thr Thr Arg Leu Leu Ser
 1               5                  10                  15

Gly His Thr Cys Phe Thr Leu Thr Gly Leu Leu Gly Thr Leu Val Thr
             20                  25                  30

Met Gly Leu Leu Thr
         35

<210> SEQ ID NO 17
<211> LENGTH: 14
<212> TYPE: PRT
<213> ORGANISM: Homo sapiens

<400> SEQUENCE: 17

Met Gly Ser Ser Lys Ser Lys Pro Lys Asp Pro Ser Gln Arg
 1               5                  10

<210> SEQ ID NO 18
<211> LENGTH: 26
<212> TYPE: PRT
<213> ORGANISM: Homo sapiens

<400> SEQUENCE: 18

Leu Leu Gln Arg Leu Phe Ser Arg Gln Asp Cys Cys Gly Asn Cys Ser
 1               5                  10                  15

Asp Ser Glu Glu Glu Leu Pro Thr Arg Leu
             20                  25

```
<210> SEQ ID NO 19
<211> LENGTH: 20
<212> TYPE: PRT
<213> ORGANISM: Rattus norvegicus

<400> SEQUENCE: 19

Lys Gln Phe Arg Asn Cys Met Leu Thr Ser Leu Cys Cys Gly Lys Asn
 1               5                  10                  15

Pro Leu Gly Asp
            20

<210> SEQ ID NO 20
<211> LENGTH: 19
<212> TYPE: PRT
<213> ORGANISM: Homo sapiens

<400> SEQUENCE: 20

Leu Asn Pro Pro Asp Glu Ser Gly Pro Gly Cys Met Ser Cys Lys Cys
 1               5                  10                  15

Val Leu Ser

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: lysosomal
      sequence.

<400> SEQUENCE: 21

Lys Phe Glu Arg Gln
 1               5

<210> SEQ ID NO 22
<211> LENGTH: 36
<212> TYPE: PRT
<213> ORGANISM: Cricetulus griseus

<400> SEQUENCE: 22

Met Leu Ile Pro Ile Ala Gly Phe Phe Ala Leu Ala Gly Leu Val Leu
 1               5                  10                  15

Ile Val Leu Ile Ala Tyr Leu Ile Gly Arg Lys Arg Ser His Ala Gly
                20                  25                  30

Tyr Gln Thr Ile
            35

<210> SEQ ID NO 23
<211> LENGTH: 35
<212> TYPE: PRT
<213> ORGANISM: Homo sapiens

<400> SEQUENCE: 23

Leu Val Pro Ile Ala Val Gly Ala Ala Leu Ala Gly Val Leu Ile Leu
 1               5                  10                  15

Val Leu Leu Ala Tyr Phe Ile Gly Leu Lys His His His Ala Gly Tyr
                20                  25                  30

Glu Gln Phe
        35

<210> SEQ ID NO 24
<211> LENGTH: 27
<212> TYPE: PRT
<213> ORGANISM: yeast
```

```
<220> FEATURE:

<400> SEQUENCE: 24

Met Leu Arg Thr Ser Ser Leu Phe Thr Arg Arg Val Gln Pro Ser Leu
 1               5                  10                  15

Phe Ser Arg Asn Ile Leu Arg Leu Gln Ser Thr
             20                  25

<210> SEQ ID NO 25
<211> LENGTH: 25
<212> TYPE: PRT
<213> ORGANISM: yeast

<400> SEQUENCE: 25

Met Leu Ser Leu Arg Gln Ser Ile Arg Phe Phe Lys Pro Ala Thr Arg
 1               5                  10                  15

Thr Leu Cys Ser Ser Arg Tyr Leu Leu
             20                  25

<210> SEQ ID NO 26
<211> LENGTH: 64
<212> TYPE: PRT
<213> ORGANISM: yeast

<400> SEQUENCE: 26

Met Phe Ser Met Leu Ser Lys Arg Trp Ala Gln Arg Thr Leu Ser Lys
 1               5                  10                  15

Ser Phe Tyr Ser Thr Ala Thr Gly Ala Ala Ser Lys Ser Gly Lys Leu
             20                  25                  30

Thr Gln Lys Leu Val Thr Ala Gly Val Ala Ala Ala Gly Ile Thr Ala
         35                  40                  45

Ser Thr Leu Leu Tyr Ala Asp Ser Leu Thr Ala Glu Ala Met Thr Ala
     50                  55                  60

<210> SEQ ID NO 27
<211> LENGTH: 41
<212> TYPE: PRT
<213> ORGANISM: yeast

<400> SEQUENCE: 27

Met Lys Ser Phe Ile Thr Arg Asn Lys Thr Ala Ile Leu Ala Thr Val
 1               5                  10                  15

Ala Ala Thr Gly Thr Ala Ile Gly Ala Tyr Tyr Tyr Tyr Asn Gln Leu
             20                  25                  30

Gln Gln Gln Gln Gln Arg Gly Lys Lys
         35                  40

<210> SEQ ID NO 28
<211> LENGTH: 4
<212> TYPE: PRT
<213> ORGANISM: Homo sapiens

<400> SEQUENCE: 28

Lys Asp Glu Leu
 1

<210> SEQ ID NO 29
<211> LENGTH: 15
<212> TYPE: PRT
<213> ORGANISM: unidentified adenovirus
<220> FEATURE:
```

```
<400> SEQUENCE: 29

Leu Tyr Leu Ser Arg Arg Ser Phe Ile Asp Glu Lys Lys Met Pro
 1               5                  10                  15

<210> SEQ ID NO 30
<211> LENGTH: 19
<212> TYPE: PRT
<213> ORGANISM: Homo sapiens

<400> SEQUENCE: 30

Leu Asn Pro Pro Asp Glu Ser Gly Pro Gly Cys Met Ser Cys Lys Cys
 1               5                  10                  15

Val Leu Ser

<210> SEQ ID NO 31
<211> LENGTH: 15
<212> TYPE: PRT
<213> ORGANISM: Homo sapiens

<400> SEQUENCE: 31

Leu Thr Glu Pro Thr Gln Pro Thr Arg Asn Gln Cys Cys Ser Asn
 1               5                  10                  15

<210> SEQ ID NO 32
<211> LENGTH: 9
<212> TYPE: PRT
<213> ORGANISM: Unknown
<220> FEATURE:
<223> OTHER INFORMATION: Description of Artificial Sequence: destruction
      sequence.

<400> SEQUENCE: 32

Arg Thr Ala Leu Gly Asp Ile Gly Asn
 1               5

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: signal
      sequence from interleukin-2.

<400> SEQUENCE: 33

Met Tyr Arg Met Gln Leu Leu Ser Cys Ile Ala Leu Ser Leu Ala Leu
 1               5                  10                  15
Val Thr Asn Ser
            20

SEQ ID NO 34
LENGTH: 29
TYPE: PRT
ORGANISM: Homo sapiens

SEQUENCE: 34

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr
            20                  25

<210> SEQ ID NO 35
<211> LENGTH: 27
<212> TYPE: PRT
<213> ORGANISM: Homo sapiens
```

-continued

```
<400> SEQUENCE: 35

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn
             20                  25

<210> SEQ ID NO 36
<211> LENGTH: 18
<212> TYPE: PRT
<213> ORGANISM: Influenza virus

<400> SEQUENCE: 36

Met Lys Ala Lys Leu Leu Val Leu Leu Tyr Ala Phe Val Ala Gly Asp
  1               5                  10                  15

Gln Ile

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: signal
      sequence from interleukin-4.

<400> SEQUENCE: 37

Met Gly Leu Thr Ser Gln Leu Leu Pro Pro Leu Phe Phe Leu Leu Ala
  1               5                  10                  15

Cys Ala Gly Asn Phe Val His Gly
             20

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: stability
      sequence.
<220> FEATURE:
<221> NAME/KEY: VARIANT
<222> LOCATION: (3)..(6)
<223> OTHER INFORMATION: The Xaa(s) at positions 3-6 can be any amino
      acid.

<400> SEQUENCE: 38

Met Gly Xaa Xaa Xaa Xaa Gly Gly Pro Pro
  1               5                  10

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: linker
      sequence.

<400> SEQUENCE: 39

Gly Ser Gly Gly Ser
  1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: linker
      sequence.
```

-continued

```
<400> SEQUENCE: 40

Gly Gly Gly Ser
  1

<210> SEQ ID NO 41
<211> LENGTH: 124
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (115)..(120)
<223> OTHER INFORMATION: The Xaa(s) at postions 115-120 can be any amino
      acid.

<400> SEQUENCE: 41

Met Arg Pro Leu Ala Gly Gly Glu His Thr Met Ala Ser Pro Leu Thr
  1               5                  10                  15

Arg Phe Leu Ser Leu Asn Leu Leu Leu Gly Glu Ser Ile Ile Leu
             20                  25                  30

Gly Ser Gly Pro Gln Arg Pro Glu Asp Cys Arg Pro Arg Gly Ser Val
         35                  40                  45

Lys Gly Thr Gly Leu Asp Phe Ala Cys Asp Ile Tyr Ile Trp Ala Pro
     50                  55                  60

Leu Ala Gly Ile Cys Val Ala Leu Leu Leu Ser Leu Ile Ile Thr Leu
 65                  70                  75                  80

Ile Cys Tyr His Ser Arg Gly Ser Gly Gly Ser Gly Ser Gly Gly Ser
                 85                  90                  95

Gly Ser Gly Gly Ser Gly Ser Gly Gly Ser Gly Ser Gly Gly Ser Gly
            100                 105                 110

Gly Gly Xaa Xaa Xaa Xaa Xaa Xaa Gly Gly Pro Pro
        115                 120

<210> SEQ ID NO 42
<211> LENGTH: 173
<212> TYPE: PRT
<213> ORGANISM: Artificial Sequence
<220> FEATURE:
<223> OTHER INFORMATION: Description of Artificial Sequence: synthetic.
<220> FEATURE:
<221> NAME/KEY: VARIANT
<222> LOCATION: (140)..(145)
<223> OTHER INFORMATION: The Xaa(s) at positions 140-145 can be any
      amino acid.

<400> SEQUENCE: 42

Met Arg Pro Leu Ala Gly Gly Glu His Thr Met Ala Ser Pro Leu Thr
  1               5                  10                  15

Arg Phe Leu Ser Leu Asn Leu Leu Leu Gly Glu Ser Ile Ile Leu
             20                  25                  30

Gly Ser Gly Pro Gln Arg Pro Glu Asp Cys Arg Pro Arg Gly Ser Val
         35                  40                  45

Lys Gly Thr Gly Leu Asp Phe Ala Cys Asp Ile Tyr Ile Trp Ala Pro
     50                  55                  60

Leu Ala Gly Ile Cys Val Ala Leu Leu Leu Ser Leu Ile Ile Thr Leu
 65                  70                  75                  80

Ile Cys Tyr His Ser Arg Gly Ser Gly Gly Ser Gly Ser Gly Gly Ser
                 85                  90                  95

Gly Ser Gly Gly Ser Gly Ser Gly Gly Ser Gly Ser Gly Gly Ser Gly
```

```
                    100                 105                 110
Gly Gly Cys Ala Ala Leu Glu Ser Glu Val Ser Ala Leu Glu Ser Glu
            115                 120                 125

Val Ala Ser Leu Glu Ser Glu Val Ala Ala Leu Xaa Xaa Xaa Xaa Xaa
        130                 135                 140

Xaa Leu Ala Ala Val Lys Ser Lys Leu Ser Ala Val Lys Ser Lys Leu
145                 150                 155                 160

Ala Ser Val Lys Ser Lys Leu Ala Ala Cys Gly Pro Pro
                165                 170
```

<210> SEQ ID NO 43
<211> LENGTH: 127
<212> TYPE: PRT
<213> ORGANISM: Artificial Sequence
<220> FEATURE:
<223> OTHER INFORMATION: Description of Artificial Sequence: synthetic.
<220> FEATURE:
<221> NAME/KEY: VARIANT
<222> LOCATION: (38)..(43)
<223> OTHER INFORMATION: The Xaa(s) at positions 38-43 can be any amino acid.

<400> SEQUENCE: 43

```
Met Arg Pro Leu Ala Gly Gly Glu His Thr Met Ala Ser Pro Leu Thr
 1               5                  10                  15

Arg Phe Leu Ser Leu Asn Leu Leu Leu Gly Glu Ser Ile Ile Leu
            20                  25                  30

Gly Ser Gly Gly Gly Xaa Xaa Xaa Xaa Xaa Xaa Gly Gly Ser Gly Gly
        35                  40                  45

Ser Gly Ser Gly Gly Ser Gly Ser Gly Gly Ser Gly Ser Gly Gly Ser
    50                  55                  60

Gly Ser Gly Gly Ser Gly Gly Pro Gln Arg Pro Glu Asp Cys Arg
65                  70                  75                  80

Pro Arg Gly Ser Val Lys Gly Thr Gly Leu Asp Phe Ala Cys Asp Ile
                85                  90                  95

Tyr Ile Trp Ala Pro Leu Ala Gly Ile Cys Val Ala Leu Leu Leu Ser
            100                 105                 110

Leu Ile Ile Thr Leu Ile Cys Tyr His Ser Arg Gly Pro Pro
        115                 120                 125
```

<210> SEQ ID NO 44
<211> LENGTH: 177
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (63)..(68)
<223> OTHER INFORMATION: The Xaa(s) at positions 63-68 can be any amino acid.

<400> SEQUENCE: 44

```
Met Arg Pro Leu Ala Gly Gly Glu His Thr Met Ala Ser Pro Leu Thr
 1               5                  10                  15

Arg Phe Leu Ser Leu Asn Leu Leu Leu Gly Glu Ser Ile Ile Leu
            20                  25                  30

Gly Ser Gly Gly Gly Cys Ala Ala Leu Glu Ser Glu Val Ser Ala Leu
        35                  40                  45

Glu Ser Glu Val Ala Ser Leu Glu Ser Glu Val Ala Ala Leu Xaa Xaa
    50                  55                  60
```

-continued

```
Xaa Xaa Xaa Xaa Leu Ala Ala Val Lys Ser Lys Leu Ser Ala Val Lys
 65                  70                  75                  80

Ser Lys Leu Ala Ser Val Lys Ser Lys Leu Ala Ala Cys Gly Gly Ser
                 85                  90                  95

Gly Gly Ser Gly Ser Gly Gly Ser Gly Gly Ser Gly Ser Gly
            100                 105                 110

Gly Ser Gly Ser Gly Ser Gly Gly Pro Gln Arg Pro Glu Asp
        115                 120                 125

Cys Arg Pro Arg Gly Ser Val Lys Gly Thr Gly Leu Asp Phe Ala Cys
130                 135                 140

Asp Ile Tyr Ile Trp Ala Pro Leu Ala Gly Ile Cys Val Ala Leu Leu
145                 150                 155                 160

Leu Ser Leu Ile Ile Thr Leu Ile Cys Tyr His Ser Arg Gly Gly Pro
                165                 170                 175

Pro
```

<210> SEQ ID NO 45
<211> LENGTH: 47
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (38)..(43)
<223> OTHER INFORMATION: The Xaa(s) at positions 38-43 can be any amino
      acid.

<400> SEQUENCE: 45

```
Met Arg Pro Leu Ala Gly Gly Glu His Arg Met Ala Ser Pro Leu Thr
  1               5                  10                  15

Arg Phe Leu Ser Leu Asn Leu Leu Leu Gly Glu Ser Ile Ile Leu
                 20                  25                  30

Gly Ser Gly Gly Gly Xaa Xaa Xaa Xaa Xaa Xaa Gly Gly Pro Pro
            35                  40                  45
```

<210> SEQ ID NO 46
<211> LENGTH: 95
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (62)..(67)
<223> OTHER INFORMATION: The Xaa(s) at positions 62-67 can be any amino
      acid.

<400> SEQUENCE: 46

```
Met Arg Pro Leu Ala Gly Gly Glu His Thr Met Ala Ser Pro Leu Thr
  1               5                  10                  15

Arg Phe Leu Ser Leu Asn Leu Leu Leu Gly Glu Ser Ile Ile Leu
                 20                  25                  30

Gly Ser Gly Gly Gly Ala Ala Leu Glu Ser Glu Val Ser Ala Leu Glu
            35                  40                  45

Ser Glu Val Ala Ser Leu Glu Ser Glu Val Ala Ala Leu Xaa Xaa Xaa
         50                  55                  60

Xaa Xaa Xaa Leu Ala Ala Val Lys Ser Lys Leu Ser Ala Val Lys Ser
 65                  70                  75                  80

Lys Leu Ala Ser Val Lys Ser Lys Leu Ala Ala Cys Gly Pro Pro
```

```
                   85                  90                  95

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (1)..(9)
<223> OTHER INFORMATION: The Xaa(s) at positions 1-3, 6, 8, 9 can be any
      amino acid.

<400> SEQUENCE: 47

Xaa Xaa Xaa Pro Pro Xaa Pro Xaa Xaa
 1               5

<210> SEQ ID NO 48
<211> LENGTH: 63
<212> TYPE: DNA
<213> ORGANISM: Artificial Sequence
<220> FEATURE:
<223> OTHER INFORMATION: Description of Artificial Sequence: synthetic
<220> FEATURE:
<221> NAME/KEY: misc_feature
<222> LOCATION: (7)..(20)
<223> OTHER INFORMATION: The n(s) at positions 7,8,10,11,13,14,16,17,
      19,20 can be any nucleic acid.

<400> SEQUENCE: 48
atgggcnnkn nknnknnknn kagacctctg cctccasbkg ggsbksbkgg aggcccacct      60
taa                                                                   63

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (3)..(16)
<223> OTHER INFORMATION: The Xaa(s) at postions 3-7, 13,15,16 can be any
      amino acid.

<400> SEQUENCE: 49

Met Gly Xaa Xaa Xaa Xaa Xaa Arg Pro Leu Pro Pro Xaa Pro Xaa Xaa
 1               5                  10                  15

Gly Gly Pro Pro
            20

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: synthetic.
<220> FEATURE:
<221> NAME/KEY: misc_feature
<222> LOCATION: (2)..(11)
<223> OTHER INFORMATION: The n(s) at positions 2-11 can be any nucleic
      acid.

<400> SEQUENCE: 50
cnnnnnnnnn nc                                                         12

<210> SEQ ID NO 51
```

```
<211> LENGTH: 17
<212> TYPE: PRT
<213> ORGANISM: Artificial Sequence
<220> FEATURE:
<223> OTHER INFORMATION: Description of Artificial Sequence: synthetic.

<400> SEQUENCE: 51

Met Gly Gly Gly Tyr Pro Tyr Asp Val Pro Asp Tyr Ala Gly Ser Leu
 1               5                  10                  15
Glx

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: synthetic.

<400> SEQUENCE: 52

Gly Lys Gln Lys Thr Lys Thr Ile Lys Gly Pro Pro
 1               5                  10

<210> SEQ ID NO 53
<211> LENGTH: 92
<212> TYPE: DNA
<213> ORGANISM: Artificial Sequence
<220> FEATURE:
<223> OTHER INFORMATION: Description of Artificial Sequence: synthetic.
<220> FEATURE:
<221> NAME/KEY: misc_feature
<222> LOCATION: (28)..(56)
<223> OTHER INFORMATION: The n(s) at postions
      28,29,31,32,34,35,37,38,40,41,43,44,46,47,49,50,52,53,55,56 can
      be any nucleic acid.

<400> SEQUENCE: 53
gcttagcaag atctctacgg tggaccknnk nnknnknnkn nknnknnknn knnknncccc    60
actcccatgg tcctacgtac caccacactg gg                                 92

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: synthetic

<400> SEQUENCE: 54
gcttagcaag atctgtgtgt cagttagggt gtgg                               34

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: synthetic.
<220> FEATURE:
<221> NAME/KEY: misc_feature
<222> LOCATION: (23)..(24)
<223> OTHER INFORMATION: The n(s) at positions 23-24 can be any nucleic
      acid.

<400> SEQUENCE: 55
ctggagaacc aggaccatgg gcnnkgggcc cccttaaacc attaaat                 47

<210> SEQ ID NO 56
<211> LENGTH: 71
<212> TYPE: DNA
```

```
<213> ORGANISM: Artificial Sequence
<220> FEATURE:
<223> OTHER INFORMATION: Description of Artificial Sequence: synthetic.
<220> FEATURE:
<221> NAME/KEY: misc_feature
<222> LOCATION: (23)..(48)
<223> OTHER INFORMATION: The n(s) at positions
      23,24,26,27,29,30,38,39,44,45,47,48 can be any
      nucleic acid.

<400> SEQUENCE: 56
ctggagaacc aggaccatgg gcnnknnknn kcctcccnnk cctnnknnkg ggcccctta      60 aaccattaaa t                                                         71

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: synthetic

<400> SEQUENCE: 57
tcatgcatcc aatttaatgg tttaag                                         26

<210> SEQ ID NO 58
<211> LENGTH: 4950
<212> TYPE: DNA
<213> ORGANISM: Artificial Sequence
<220> FEATURE:
<223> OTHER INFORMATION: Description of Artificial Sequence: synthetic.

<400> SEQUENCE: 58
tgaaagaccc cacctgtagg tttggcaagc tagcttaagt aacgccattt tgcaaggcat    60
ggaaaataca taactgagaa tagagaagtt cagatcaagg ttaggaacag agagacagca   120
gaatatgggc caaacaggat atctgtggta agcagttcct gccccggctc agggccaaga   180
acagatggtc cccagatgcg gtcccgccct cagcagtttc tagagaacca tcagatgttt   240
ccagggtgcc ccaaggacct gaaaatgacc ctgtgcctta tttgaactaa ccaatcagtt   300
cgcttctcgc ttctgttcgc gcgcttctgc tccccgagct caataaaaga gcccacaacc   360
cctcactcgg cgcgccagtc ctccgataga ctgcgtcgcc cgggtacccg tattcccaat   420
aaagcctctt gctgtttgca tccgaatcgt ggactcgctg atccttggga gggtctcctc   480
agattgattg actgcccacc tcggggtct  ttcatttgga ggttccaccg agatttggag   540 accccctgcct agggaccacc gacccccccg ccgggaggta agctggccag cggtcgtttc   600
ctgtctgtct ctgtctttgt gcgtgtttgt gccggcatct aatgtttgcg cctgcgtctg   660
tactagttag ctaactagct ctgtatctgg cggacccgtg gtggaactga cgagttctga   720
acacccggcc gcaaccctgg gagacgtccc agggactttg ggggccgttt tgtggcccg   780 acctgaggaa gggagtcgat gtggaatccg accccgtcag gatatgtggt tctggtagga   840
gacgagaacc taaaacagtt cccgcctccg tctgaatttt tgctttcggt ttggaaccga   900
agccgcgcgt cttgtctgct gcagcgctgc agcatcgttc tgtgttctct ctgtctgact   960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtcccctac atcgtgacct gggaagcctt ggcttttgac   1260
```

-continued

```
cccctccct gggtcaagcc ctttgtacac cctaagcctc cgcctcctct tcctccatcc    1320
gccccgtctc tccccttga acctcctcgt tcgaccccgc ctcgatcctc cctttatcca    1380
gccctcactc cttctctagg cgccggaatt ccaggaccat gggcgggccc ccttaaacca   1440
ttaaattggt aaaataaagg atccgtcgac ctgcagccaa gcttatcgat aaaataaaag   1500
attttattta gtctccagaa aaggggggga atgaaagacc ccacctgtag gtttggcaag   1560
ctagcttaag taacgccatt ttgcaaggca tggaaaatac ataactgaga atagagaagt   1620
tcagatcaag gttaggaaca gagagacagc agaatatggg ccaaacagga tatctgtggt   1680
aagcagttcc tgccccggct cagggccaag aacagatggt ccccagatgc ggtcccgccc   1740
tcagcagttt ctagagaacc atcagatgtt tccagggtgc cccaaggacc tgaaaatgac   1800
cctgtgcctt atttgaacta accaatcagt tcgcttctcg cttctgttcg cgcgcttctg   1860
ctccccgagc tcaataaaag agcccacaac ccctcactcg gcgcgccagt cctccgatag   1920
actgcgtcgc ccgggtaccc gtgtatccaa taaaccctct tgcagttgca tccgacttgt   1980
ggtctcgctg ttccttggga gggtctcctc tgagtgattg actacccgtc agcggggtc   2040
tttcattcgt aatcatggtc atagctgttt cctgtgtgaa attgttatcc gctcacaatt   2100
ccacacaaca tacgagccgg aagcataaag tgtaaagcct ggggtgccta atgagtgagc   2160
taactcacat taattgcgtt gcgctcactg cccgctttcc agtcgggaaa cctgtcgtgc   2220
cagctgcatt aatgaatcgg ccaacgcgcg gggagaggcg gtttgcgtat tgggcgctct   2280
tccgcttcct cgctcactga ctcgctgcgc tcggtcgttc ggctgcggcg agcggtatca   2340
gctcactcaa aggcggtaat acggttatcc acagaatcag gggataacgc aggaaagaac   2400
atgtgagcaa aaggccagca aaaggccagg aaccgtaaaa aggccgcgtt gctggcgttt   2460
ttccataggc tccgcccccc tgacgagcat cacaaaaatc gacgctcaag tcagaggtgg   2520
cgaaacccga caggactata agataccag gcgtttcccc ctggaagctc cctcgtgcgc    2580
tctcctgttc cgaccctgcc gcttaccgga tacctgtccg cctttctccc ttcgggaagc   2640
gtggcgcttt ctcatagctc acgctgtagg tatctcagtt cggtgtaggt cgttcgctcc   2700
aagctgggct gtgtgcacga accccccgtt cagcccgacc gctgcgcctt atccggtaac   2760
tatcgtcttg agtccaaccc ggtaagacac gacttatcgc cactggcagc agccactggt   2820
aacaggatta gcagagcgag gtatgtaggc ggtgctacag agttcttgaa gtggtggcct   2880
aactacggct acactagaag gacagtattt ggtatctgcg ctctgctgaa gccagttacc   2940
ttcggaaaaa gagttggtag ctcttgatcc ggcaaacaaa ccaccgctgg tagcggtggt   3000
ttttttgttt gcaagcagca gattacgcgc agaaaaaaag gatctcaaga agatcctttg   3060
atcttttcta cggggtctga cgctcagtgg aacgaaaact cacgttaagg gattttggtc   3120
atgagattat caaaaaggat cttcacctag atccttttaa attaaaaatg aagttttaaa   3180
tcaatctaaa gtatatatga gtaaacttgg tctgacagtt accaatgctt aatcagtgag   3240
gcacctatct cagcgatctg tctatttcgt tcatccatag ttgcctgact ccccgtcgtg   3300
tagataacta cgatacggga gggcttacca tctggcccca gtgctgcaat gataccgcga   3360
gacccacgct caccggctcc agatttatca gcaataaacc agccagccgg aagggccgag   3420
cgcagaagtg gtcctgcaac tttatccgcc tccatccagt ctattaattg ttgccgggaa   3480
gctagagtaa gtagttcgcc agttaatagt ttgcgcaacg ttgttgccat tgctacaggc   3540
atcgtggtgt cacgctcgtc gtttggtatg gcttcattca gctccggttc caacgatca   3600
```

```
aggcgagtta catgatcccc catgttgtgc aaaaaagcgg ttagctcctt cggtcctccg      3660
atcgttgtca gaagtaagtt ggccgcagtg ttatcactca tggttatggc agcactgcat      3720
aattctctta ctgtcatgcc atccgtaaga tgcttttctg tgactggtga gtactcaacc      3780
aagtcattct gagaatagtg tatgcggcga ccgagttgct cttgcccggc gtcaatacgg      3840
gataataccg cgccacatag cagaacttta aaagtgctca tcattggaaa acgttcttcg      3900
gggcgaaaac tctcaaggat cttaccgctg ttgagatcca gttcgatgta acccactcgt      3960
gcacccaact gatcttcagc atctttact ttcaccagcg tttctgggtg agcaaaaaca      4020
ggaaggcaaa atgccgcaaa aagggaata agggcgacac ggaaatgttg aatactcata      4080
ctcttccttt ttcaatatta ttgaagcatt tatcagggtt attgtctcat gagcggatac      4140
atatttgaat gtatttagaa aaataaacaa atagggttc cgcgcacatt tccccgaaaa      4200
gtgccacctg acgtctaaga accattatt atcatgacat taacctataa aaataggcgt      4260
atcacgaggc cctttcgtct cgcgcgtttc ggtgatgacg tgaaaacct ctgacacatg      4320 cagctcccgg agacggtcac agcttgtctg taagcggatg ccgggagcag acaagcccgt      4380
cagggcgcgt cagcgggtgt tggcgggtgt cggggctggc ttaactatgc ggcatcagag      4440
cagattgtac tgagagtgca ccatatgcgg tgtgaaatac cgcacagatg cgtaaggaga      4500
aaataccgca tcaggcgcca ttcgccattc aggctgcgca actgttggga agggcgatcg      4560
gtgcgggcct cttcgctatt acgccagctg gcgaaagggg gatgtgctgc aaggcgatta      4620
agttgggtaa cgccagggtt ttcccagtca cgacgttgta aaacgacggc cagtgccacg      4680
ctctccctta tgcgactcct gcattaggaa gcagcccagt agtaggttga ggccgttgag      4740
caccgccgcc gcaaggaatg gtgcatgcaa ggagatggcg cccaacagtc ccccggccac      4800
ggggcctgcc accatacccca cgccgaaaca gcgctcatg agcccgaagt ggcgagcccg      4860
atcttcccca tcggtgatgt cggcgatata ggcgccagca accgcacctg tggcgccggt      4920
gatgccggcc acgatgcgtc cggcgtagag                                       4950
```

<210> SEQ ID NO 59
<211> LENGTH: 74
<212> TYPE: DNA
<213> ORGANISM: Artificial Sequence
<220> FEATURE:
<223> OTHER INFORMATION: Description of Artificial Sequence: synthetic

<400> SEQUENCE: 59

```
ctggagaacc aggaccatgg gcaagagaaa gggcgatgag gtggatggag tggggccccc      60
ttaaaccatt aaat                                                        74
```

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: synthetic.

<400> SEQUENCE: 60

```
Met Gly Lys Arg Lys Gly Asp Glu Val Asp Gly Val Gly Pro Pro
 1               5                  10                  15
```

<210> SEQ ID NO 61
<211> LENGTH: 74
<212> TYPE: DNA
<213> ORGANISM: Artificial Sequence
<220> FEATURE:

-continued

```
<223> OTHER INFORMATION: Description of Artificial Sequence: synthetic.
<220> FEATURE:
<221> NAME/KEY: misc_feature
<222> LOCATION: (35)..(48)
<223> OTHER INFORMATION: The n(s) at positions 35,36,38,39,41,42,47,48
      can be any nucleic acid.

<400> SEQUENCE: 61
ctggagaacc aggaccatgg gcaagagaaa gggcnnknnk nnkgaknnkg tggggccccc        60
ttaaaccatt aaat                                                         74

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: random
      sequence.
<220> FEATURE:
<221> NAME/KEY: VARIANT
<222> LOCATION: (7)..(12)
<223> OTHER INFORMATION: The Xaa(s) at postions 7-9,12 can be any amino
      acid.

<400> SEQUENCE: 62

Met Gly Lys Arg Lys Gly Xaa Xaa Xaa Asp Glu Xaa Val Gly Pro Pro
 1               5                  10                  15

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: synthetic

<400> SEQUENCE: 63
tcatgcatcc aatttaatgg tttaag                                            26

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 64
gatcctccct ttatccag                                                     18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 65
ctacaggtgg ggtctttc                                                     18

<210> SEQ ID NO 66
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 66
atgggcaaga gaaagggcac ggcgtctgat gctgtggggc cccttaa                     48
```

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 67

Thr Ala Ser Asp Ala
 1               5

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 68
atgggcaaga gaaagggcta tccttctgat gtggtggggc ccccttaa        48

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 69

Tyr Pro Ser Asp Val
 1               5

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 70
atgggcaaga gaaagggcac gccttcggat atggtggggc ccccttaa        48

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 71

Thr Pro Ser Asp Met
 1               5

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 72
atgggcaaga gaaagggcac ggcttctgat cttgtggggc ccccttaa        48

<210> SEQ ID NO 73
<211> LENGTH: 5

```
<212> TYPE: PRT
<213> ORGANISM: Artificial Sequence
<220> FEATURE:
<223> OTHER INFORMATION: Description of Artificial Sequence: synthetic

<400> SEQUENCE: 73

Thr Ala Ser Asp Leu
 1               5

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 74
atgggcaaga gaaagggctc tgatagggat attgtgggc ccccttaa                    48

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 75

Ser Asp Arg Asp Ile
 1               5

<210> SEQ ID NO 76
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 76
atgggcaaga gaaagggctg gttgctagag tttgtgggc ccccttaa                    48

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 77

Trp Leu Leu Glu Phe
 1               5

<210> SEQ ID NO 78
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 78
atgggcaaga gaaagggctg gttgatagag tttgtgggc ccccttaa                    48

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: synthetic
```

<400> SEQUENCE: 79

Trp Leu Ile Glu Phe
 1               5

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: synthetic

<400> SEQUENCE: 80
atgggcaaga gaaagggctg gttgctagag tttgtggggc cccctaa         48

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 81

Ser Tyr Gln Asp Leu
 1               5

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: VARIANT
<222> LOCATION: (3)..(12)
<223> OTHER INFORMATION: The Xaa(s) at positions 3-12 can be any amino
      acid.

<400> SEQUENCE: 82

Met Gly Xaa Xaa Xaa Xaa Xaa Xaa Xaa Xaa Xaa Xaa Gly Gly Pro Pro
 1               5                  10                  15

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 83
ctgacacaca ttccacag                                            18

<210> SEQ ID NO 84
<211> LENGTH: 122
<212> TYPE: DNA
<213> ORGANISM: Artificial Sequence
<220> FEATURE:
<223> OTHER INFORMATION: Description of Artificial Sequence: synthetic

<400> SEQUENCE: 84
ggatccagtg tggtggtacg taggaatacc atgggatgtc cgtctgttgc taggccgcgg    60
ggtggtgggg gccccccta gctaactaaa gatcccagtg tggtggtacg taggaattcg   120
cc                                                                 122

<210> SEQ ID NO 85

<211> LENGTH: 16
<212> TYPE: PRT
<213> ORGANISM: Artificial Sequence
<220> FEATURE:
<223> OTHER INFORMATION: Description of Artificial Sequence: synthetic

<400> SEQUENCE: 85

Met Gly Cys Pro Ser Val Ala Arg Pro Arg Gly Gly Gly Pro Pro
 1               5                  10                  15

<210> SEQ ID NO 86
<211> LENGTH: 113
<212> TYPE: DNA
<213> ORGANISM: Artificial Sequence
<220> FEATURE:
<223> OTHER INFORMATION: Description of Artificial Sequence: synthetic

<400> SEQUENCE: 86
ggatcccagt gtggtggtac gtaggaatac catgggattg tcttttgtta ttctgtctgc    60
agcatcgtgg gggcccccccc tagctaacta aagatcccag tgtggtggta cgt          113

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: synthetic

<400> SEQUENCE: 87

Met Gly Leu Ser Phe Val Ile Leu Ser Ala Ala Ser Trp Gly Pro Pro
 1               5                  10                  15

<210> SEQ ID NO 88
<211> LENGTH: 96
<212> TYPE: DNA
<213> ORGANISM: Artificial Sequence
<220> FEATURE:
<223> OTHER INFORMATION: Description of Artificial Sequence: synthetic

<400> SEQUENCE: 88
ggatcccagt gtggtggtac gtaggagtac catgggacct ccgatttggt atactcattg    60
gagtcatggg ggcccccccct agctaactaa agatcc                              96

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: synthetic

<400> SEQUENCE: 89

Met Gly Pro Pro Ile Trp Tyr Thr His Trp Ser His Gly Gly Pro Pro
 1               5                  10                  15

<210> SEQ ID NO 90
<211> LENGTH: 95
<212> TYPE: DNA
<213> ORGANISM: Artificial Sequence
<220> FEATURE:
<223> OTHER INFORMATION: Description of Artificial Sequence: synthetic

<400> SEQUENCE: 90
ggatcccagt gtggtggtac gtaggagtac catggaagtc aggcgtttgt gaatactcgg    60 cataagggggg gcccccccta gctaactaaa gatcc                               95

```
<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 91

Met Glu Val Arg Arg Leu
  1               5

<210> SEQ ID NO 92
<211> LENGTH: 126
<212> TYPE: DNA
<213> ORGANISM: Artificial Sequence
<220> FEATURE:
<223> OTHER INFORMATION: Description of Artificial Sequence: synthetic

<400> SEQUENCE: 92
ccggccgtat tcaacaaggg gctgaaggat gcccagaagg taccccattg tatgggatct      60
gatctggggc ctcggtgcac atgctttaca tgtgtttagt cgaggttaaa aaacgtctag    120
gccccc                                                               126

<210> SEQ ID NO 93
<211> LENGTH: 107
<212> TYPE: DNA
<213> ORGANISM: Artificial Sequence
<220> FEATURE:
<223> OTHER INFORMATION: Description of Artificial Sequence: synthetic

<400> SEQUENCE: 93
ggatcccagt gtggtggtac gtaggaatac catgggactt tagccgggcc cccctagct      60 aactaaagat cccagtgtgg tggtacgtag gaattcgcca gcacagt                  107

<210> SEQ ID NO 94
<211> LENGTH: 95
<212> TYPE: DNA
<213> ORGANISM: Artificial Sequence
<220> FEATURE:
<223> OTHER INFORMATION: Description of Artificial Sequence: synthetic

<400> SEQUENCE: 94
ggatcccagt gtggtggtac gtaggaatac atgggaactg ttatggcgat gtcggattag      60
gtcgaggggg gccccccta gctaactaaa gatcc                                  95

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 95

Met Gly Thr Val Met Ala Met Ser Asp
  1               5

<210> SEQ ID NO 96
<211> LENGTH: 95
<212> TYPE: DNA
<213> ORGANISM: Artificial Sequence
<220> FEATURE:
<223> OTHER INFORMATION: Description of Artificial Sequence: synthetic

<400> SEQUENCE: 96
```

```
ggatccagtg tggtggtacg taggaatacc atgggatgtc cgtctgttgc taggccgcgg      60
ggtggtgggg gcccccccta gctaactaaa gatcc                                 95
```

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: synthetic

<400> SEQUENCE: 97

```
Met Gly Cys Pro Ser Val Ala Arg Pro Arg Gly Gly Gly Gly Pro Pro
 1               5                  10                  15
```

METHODS FOR SCREENING FOR TRANSDOMINANT EFFECTOR PEPTIDES AND RNA MOLECULES

FIELD OF THE INVENTION

The technical field of this invention is methods for screening for transdominant effector peptides and RNA molecules selected inside living cells from randomized pools.

BACKGROUND OF THE INVENTION

Signaling pathways in cells often begin with an effector stimulus that leads to a phenotypically describable change in cellular physiology. Despite the key role intracellular signaling pathways play in disease pathogenesis, in most cases, little is understood about a signaling pathway other than the initial stimulus and the ultimate cellular response.

Historically, signal transduction has been analyzed by biochemistry or genetics. The biochemical approach dissects a pathway in a "stepping-stone" fashion: find a molecule that acts at, or is involved in, one end of the pathway, isolate assayable quantities and then try to determine the next molecule in the pathway, either upstream or downstream of the isolated one. The genetic approach is classically a "shot in the dark": induce or derive mutants in a signaling pathway and map the locus by genetic crosses or complement the mutation with a cDNA library. Limitations of biochemical approaches include a reliance on a significant amount of pre-existing knowledge about the constituents under study and the need to carry such studies out in vitro, post-mortem. Limitations of purely genetic approaches include the need to first derive and then characterize the pathway before proceeding with identifying and cloning the gene.

Screening molecular libraries of chemical compounds for drugs that regulate signal systems has led to important discoveries of great clinical significance. Cyclosporin A (CsA) and FK506, for examples, were selected in standard pharmaceutical screens for inhibition of T-cell activation. It is noteworthy that while these two drugs bind completely different cellular proteins—cyclophilin and FK506 binding protein (FKBP), respectively, the effect of either drug is virtually the same—profound and specific suppression of T-cell activation, phenotypically observable in T cells as inhibition of mRNA production dependent on transcription factors such as NF-AT and NF-κB. Libraries of small peptides have also been successfully screened in vitro in assays for bioactivity. The literature is replete with examples of small peptides capable of modulating a wide variety of signaling pathways. For example, a peptide derived from the HIV-1 envelope protein has been shown to block the action of cellular calmodulin.

A major limitation of conventional in vitro screens is delivery. While only minute amounts of an agent may be necessary to modulate a particular cellular response, delivering such an amount to the requisite subcellular location necessitates exposing the target cell or system to relatively massive concentrations of the agent. The effect of such concentrations may well mask or preclude the targeted response.

Thus, it is an object of the present invention to provide methods and compositions for the effective introduction of random libraries into cells to screen for bioactive compounds.

Relevant Literature

Mann et al. (1983) Cell 33, 153–159, Pear et al. (1993) Proc. Natl. Acad. Sci. USA 90(18):8392–6 and WO 94/19478 describe the BOSC and BING retroviral systems useful as delivery vectors for the disclosed methods.

Scott and Craig (1994) Current Opinion in Biotechnology 5:40–48 review random peptide libraries. Hupp et al. (1995) describe small peptides which activate the latent sequence-specific DNA binding function of p53. Palzkill et al. (1994) report the selection of functional signal cleavage sites from a library of random sequences introduced into TEM-1-lactamase.

SUMMARY OF THE INVENTION

The invention provides methods and compositions for screening for transdominant bioactive agents such as pharmaceuticals. The invention accesses molecules or targets within living cells and provides for the direct selection of those bioactive agents with desired phenotypic effects.

In one aspect of the invention, methods for screening for a transdominant bioactive agent capable of altering the phenotype of a cell are provided. The methods comprise the steps of a) introducing a molecular library of randomized candidate nucleic acids into a plurality of cells, wherein each of said nucleic acids comprises a different nucleotide sequence; b) screening the plurality of cells for a cell exhibiting an altered phenotype, wherein the altered phenotype is due to the presence of a transdominant bioactive agent. The methods may also include the steps of c) isolating the cell(s) exhibiting an altered phenotype, d) isolating a candidate nucleic acid from the cell(s).

The invention further provides methods for isolating a target molecule using either a candidate nucleic acid or the expression product of a candidate nucleic acid.

In an additional aspect, the candidate nucleic acids of the invention are linked to fusion partners.

In a further aspect, the invention provides methods for screening for a transdominant bioactive agent capable of altering the phenotype of a cell. The methods comprises the steps of a) introducing a molecular library of randomized candidate nucleic acids into a first plurality of cells, wherein each of the nucleic acids comprises a different nucleotide sequence; b) contacting the first plurality of cells with a second plurality of cells; and c) screening the second plurality of cells for a cell exhibiting an altered phenotype.

In an additional aspect, the present invention provides molecular libraries of retroviruses comprising different randomized nucleic acids, and cellular libraries containing the retroviral libraries.

BRIEF DESCRIPTION OF THE FIGURES

FIG. 1. Creation of a library of random peptides in a retrovirus DNA construct by PCR.

FIG. 2 (SEQ ID NOS:1–3). Creation of a library of random peptides in a retrovirus DNA construct by primed DNA synthesis.

FIGS. 3A–3C. Presentation constructs for localizing presentation structures to specific cellular locales.

FIG. 4. Schematic of a retroviral construct.

DETAILED DESCRIPTION OF THE INVENTION

The present invention provides methods and compositions to create, effectively introduce into cells and screen compounds that affect a signaling pathway. Little or no knowledge of the pathway is required, other than a presumed signaling event and an observable physiologic change in the target cell. The disclosed methods are conceptually distinct from prior library search methods in that it is an in vivo stratagem for accessing intracellular signaling mechanisms. The invention also provides for the isolation of the constituents of the pathway, the tools to characterize the pathway, and lead compounds for pharmaceutical development.

The present invention provides methods for the screening of candidate bioactive agents which are capable of altering the phenotype of cells containing the agents. The methods of the present invention provide a significant improvement over conventional screening techniques, as they allow the rapid screening of large numbers of random oligonucleotides and their corresponding expression products in a single, in vivo step. Thus, by delivering the random oligonucleotides to cells and screening the same cells, without the need to collect or synthesize in vitro the candidate agents, highly efficient screening is accomplished. In addition, the present methods allow screening in the absence of significant prior characterization of the cellular defect per se.

Thus, the present invention provides methods for screening candidate bioactive agents for a transdominant bioactive agent capable of altering the phenotype of a cell.

By "candidate bioactive agents" or "candidate drugs" or "candidate expression products" or grammatical equivalents herein is meant the expression product of a candidate nucleic acid which may be tested for the ability to transdominantly alter the phenotype of a cell. As is described below, the candidate bioactive agents are the expression products of candidate nucleic acids, and encompass several chemical classes, including peptides and nucleic acids such as DNA, messenger RNA (mRNA), antisense RNA, ribozyme components, etc. Thus, the candidate bioactive agents (expression products) may be either translation products of the candidate nucleic acids, i.e. peptides, or transcription products of the candidate nucleic acids, i.e. either DNA or RNA.

In a preferred embodiment, the candidate bioactive agents are translation products of the candidate nucleic acids. In this embodiment, the candidate nucleic acids are introduced into the cells, and the cells express the nucleic acids to form peptides. Thus, in this embodiment, the candidate bioactive agents are peptides. Generally, peptides ranging from about 4 amino acids in length to about 100 amino acids may be used, with peptides ranging from about 5 to about 50 being preferred, with from about 5 to about 30 being particularly preferred and from about 6 to about 20 being especially preferred.

In a preferred embodiment, the candidate bioactive agents are transcription products of the candidate nucleic acids, and are thus also nucleic acids. The transcription products may be either primary transcripts or secondary translation products. That is, using the retroviral reverse transcriptase, primary DNA is made which are later converted into double stranded DNA. Additionally, using the primary DNA, RNA transcripts can be generated within the cell, including mRNA, antisense RNA and ribozymes or portions thereof.

At a minimum, the candidate bioactive agents comprise randomized expression products of the candidate nucleic acids. That is, every candidate bioactive agent has a randomized portion, as defined herein, that is the basis of the screening methods outlined herein. In addition, to the randomized portion, the candidate bioactive agent may also include a fusion partner.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference, and FIGS. 3A–3C). Using this system investigators have isolated peptides capable of high affinity interaction with the appropriate target. In general, coiled-coil structures allow for between 6 to 20 randomized positions.

A preferred coiled-coil presentation structure is as follows: MGCAALESEVSALESEVASLESEVAAL GRGDMPLAAVKSKLSAVKSKLASVKSKLAACGPP (SEQ ID NO:4). The underlined regions represent a coiled-coil leucine zipper region defined previously (see Martin et al., EMBO J. 13(22):5303–5309 (1994), incorporated by reference). The bolded GRGDMP (SEQ ID NO:5) region represents the loop structure and when appropriately replaced with randomized peptides (i.e. candidate bioactive agents, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

A preferred minibody presentation structure is as follows: MGRNSQATSGFTFSHFYMEWVRGGEYIAASR HKHNKYTTEYSASVKGRYIVSRDTSQSILYLQKKK GPP (SEQ ID NO:6). The bold, underline regions are the regions which may be randomized. The italicized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLSs such as that of the SV40 (monkey virus) large T Antigen (Pro Lys Lys Lys Arg Lys Val (SEQ ID NO:7)), Kalderon (1984), et al., Cell, 39:499–509; the human retinoic acid receptor-β nuclear localization signal (ARRRRP (SEQ ID NO:8)); NFκB p50 (EEVQRKRQKL (SEQ ID NO:9)); Ghosh et al., Cell 62:1019 (1990); NFκB p65 (EEKRKRTYE (SEQ ID NO:10)); Nolan et al., Cell 64:961 (1991); and others (see for example Boulikas, J. Cell. Biochem. 55(1):32–58 (1994), hereby incorporated by reference) and double basic NLSs exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp (SEQ ID NO:11)), Dingwall, et al., Cell, 30:449–458,1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space; see FIGS. 3A–3C. For extracellular presentation, a membrane anchoring region is provided at the carboxyl terminus of the peptide presentation structure. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960-1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2-28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:12); Nakauchi et al., PNAS USA 82:5126 (1985)) and 1-21 in the case of ICAM-2 (MSSFGYRTLTVALFTLIC-CPG (SEQ ID NO:13); Staunton et al., Nature (London) 339:61 (1989)). These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPEDC- RPRGSVKGTGLDFACDIYIWA-PLAGICVALLLSLIITLICYHSR (SEQ ID NO: 14); Nakauchi, supra) and 224–256 from ICAM-2 (MVIIVTVVSVLLSLFVTSVLLCFIFGQHLRQQR (SEQ ID NO:15); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO:16), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:17; see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSD-SEEELPTRL (SEQ ID NO:18), with the bold cysteines being palmitolyated; Stoffel et al., J. Biol. Chem 269:27791 (1994)); from rhodopsin (KQFRNCMLTSLCCGKNPLGD (SEQ ID NO:19); Barnstable et al., J. Mol. Neurosci. 5(3):207 (1994)); and the p21 H-ras 1 protein (LNPPDESGPGCMSCKCVLS (SEQ ID NO:20); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:21); Dice, Ann. N.Y. Acad. Sci. 674:58 (1992); or lysosomal membrane sequences from Lamp-1 (MLIPIAGFFALAGLVLIVLIAYLIGRKRSHAGYQTI (SEQ ID NO:22), Uthayakumar et al., Cell. Mol. Biol. Res. 41:405 (1995)) or Lamp-2 (LVPIAVGAALAGVLILVL-LAYFIGLKHHHAGYEQF (SEQ ID NO:23), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:24); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:25);

Schatz, supra); mitochondrial intermembrane space sequences (yeast cytochrome c1; MFSMLSKR-WAQRTLSKSFYSTATGAASKSGKLTQKLVTAGVAAA-GITASTLLYADSLTAEAMTA (SEQ ID NO:26); Schatz, supra) or mitochondrial outer membrane sequences (yeast 70 kD outer membrane protein; MKSFITRNKTAIL-ATVAATGTAIGAYYYYNQLQQQQQRGKK (SEQ ID NO:27); Schatz, supra).

The target sequences may also be endoplasmic reticulum sequences, including the sequences from calreticulin (KDEL (SEQ ID NO:28); Pelham, Royal Society London Transactions B; 1–10 (1992)) or adenovirus E3/19K protein (LYLSRRSFIDEKKMP (SEQ ID NO:29); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO:30, with the bold cysteine farnesylated; Capon, supra); geranylgeranylation sequences (for example, protein rab-5A; LTEPTQPTRNQCCSN (SEQ ID NO:31), with the bold cysteines geranylgeranylated; Farnsworth, PNAS USA 91:11963 (1994)); or destruction sequences (cyclin B1; RTALGDIGN (SEQ ID NO:32); Klotzbucher et al., EMBO J. 1:3053 (1996)).

In a preferred embodiment, the targeting sequence is a secretory signal sequence capable of effecting the secretion of the candidate translation product. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure, see FIGS. 3A–3C. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:33); Villinger et al., J. Immunol. 155:3946 (1995)), growth hormone (MATGSRTSLLLAFGLLCLPWL-QEGSAFPT (SEQ ID NO:34); Roskam et al., Nucleic Acids Res. 7:30 (1979)); preproinsulin (MALWMRLLPLLAL-LALWGPDPAAAFVN (SEQ ID NO:35); Bell et al., Nature 284:26 (1980)); and influenza HA protein (MKAKLLVLLYAFVAGDQI (SEQ ID NO:36); Sekikawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows: MGLTSQLLPPLFFLLA-CAGNFVHG (SEQ ID NO:37).

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: $MG(X)_nGGPP$ (SEQ ID NO:38), where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein—protein interaction sites are known. In addition, dimerization sequences may also be elucidated using standard methods such as the yeast two hybrid system, traditional biochemical affinity binding studies, or even using the present methods.

The fusion partners may be placed anywhere (i.e. N-terminal, C-terminal, internal) in the structure as the biology and activity permits.

In a preferred embodiment, the fusion partner includes a linker or tethering sequence. Linker sequences between various targeting sequences (for example, membrane targeting sequences) and the other components of the constructs (such as the randomized candidate agents) may be desirable to allow the candidate agents to interact with potential targets unhindered. For example, when the candidate bioactive agent is a peptide, useful linkers include glycine-serine polymers (including, for example, (GS)$_n$, (GSGGS)$_n$ (SEQ ID NO:39) and (GGGS)$_n$ (SEQ ID NO:40), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences. As is more fully described below, using a base vector that contains a cloning site for receiving random and/or biased libraries, one can cassette in various fusion partners 5' and 3' of the library. Table 1 outlines some of the possible combinations (without specifying the presentation structures) as follows. Using V as the variable cloning site for the random nucleic acid libraries, and representing each fusion partner by another letter, (i.e. N for nuclear localization sequence) each construct can be named as a string of representative letters reading 5' to 3' read as nucleic acid or N-terminal to C-terminal read as protein, such as NV or if cloned downstream of the variable region, VN. As implied here, the fusion partner sequences are cloned as cassettes into sites on either side of the variable region. C is for cytoplasmic (i.e. no localization sequence), E is a rescue sequence such as the myc epitope, G is a linker sequence (G10 is a glycine-serine chain of 10 amino acids, and G20 is a glycine-serine chain of 20 amino acids), M is a myristylation sequence, N is a nuclear localization sequence, ssTM is the signal sequence for a transmembrane anchoring sequence, TM is the transmembrane anchoring sequence, GPI is a GPI membrane anchor sequence; S is a secretory signal sequence, etc. As will be appreciated by those in the art, any number of combinations can be made, in addition to those listed below.

TABLE 1

| | |
|---|---|
| cytoplasmic | C V |
| | C E V |
| | C V E |
| secreted | S V |
| | S E V |
| | S V E |

TABLE 1-continued

| | |
|---|---|
| myristylated | M V |
| | M E V |
| | M E G20 V |
| transmembrane (intracellular) | ssTM V |
| | ssTM V TM |
| | ssTM V E TM |
| | ssTM V G20 E TM |
| | ssTM V E |
| transmembrane (GPI linked) | ssTM V G E TM |
| nuclear localization | N E V |
| | N V E |

As will be appreciated by those in the art, these modules of sequences can be used in a large number of combinations and variations. In addition, as discussed herein, it is possible to have more than one variable region in a construct, either to together form a new surface or to bring two other molecules together.

In a preferred embodiment, a candidate bioactive agent linked to a presentation structure is added at the variable region cloning site, V, above. Alternatively, no presentation structure is used, giving a "free" or "non-constrained" peptide or expression product.

Preferred embodiments include the following:

a) intracellular, membrane-anchored, linked (i.e. tethered) free peptide: MRPLAGGEHTMASPLTRFLSLN LL LLGESIILGSGPQRPEDCRPRGSVKGTGLDFACDIY IWAPLAGICVALLLSLIITLICYHSR-GSGGSGSGGSGS-GGSGSGGSGSGGSGGG-(X)$_n$-GGPP (SEQ ID NO:41), with the secretion signal from murine CD8 in bold, the transmembrane region of CD8 in underline, and the linker, to provide flexibility (glycine) and solubility (serine) in italics. (X)$_n$ represents the random peptide, where n is an interger greater than about six. A preferred embodiment utilizing this structure utilizes biased peptides, as described below, for example using biased SH-3 domain-binding peptide libraries in the non-constrained peptide structures, since a number of surface receptor signaling systems employ SH-3 domains as part of the signaling apparatus.

b) intracellular, membrane-achored, linked coiled coil: MRPLAGGEHTMASPLTRFLSLN L LLLGESIILGSGPQRPEDCRPRGSVKGTGLDFACDIY IWAPLAGICVALLLSLIITLICYHSRGSGGSGSGGSGSG GSGSGGSGSGGSGGGCAALESEVSALESEVASLESEV AAL-(X)$_n$-LAAVKSKLSAVKSKLASVKSKLAACGPP (SEQ ID NO:42), with the coiled-coil structure shown in underlined italics.

c) surface-tethered extracellular, non-constrained:

MRPLAGGEHTMASPLTRFLSLNLLLLGESIILGSGGG-(X)$_n$- (SEQ ID NO:43)

*GGSGGSGSGGSGSGGSGSGGSGSGGSGGGPQRPEDCRPRGSVKGTGLDFACDIYIWAPLAGICV*

ALLLSLIITLICYHSRGGPP.

d) surface-tethered, extracellular constrained:

MRPLAGGEHTMASPLTRFLSLNLLLLGESIILGSGGGC (SEQ ID NO:44)
AALESEVSALESEVASLESEVAAL-(X)$_n$-

*LAAVKSKLSAVKSKLASVKSKLAACEE GGSGGSGSGGSGSGGSGSGGSGSGGSGGGPQRPEDCRPR*

*GSVKGTGLDFACDIYIWAPLAGICVALLLSLIITLICYHSRGGPP.* e) secreted, non-constrained: MRPLAGGEHT-MASPLTRFLSLNLLLLGESIILGSGGG-(X)$_n$-GGPP (SEQ ID NO:45).

f) secreted, constrained:

MRPLAGGEHTMASPLTRFLSLNLLLLGESIILGSGGGAALESEVSALESEVASLESEVAAL-(X)$_n$- (SEQ ID NO:46)

LAAVKSKLSAVKSKLASVKSKLAACGPP.

The candidate bioactive agents as described above are encoded by candidate nucleic acids. By "candidate nucleic acids" herein is meant a nucleic acid, generally RNA when retroviral delivery vehicles are used, which can be expressed to form candidate bioactive agents; that is, the candidate nucleic acids encode the candidate bioactive agents and the fusion partners, if present. In addition, the candidate nucleic acids will also generally contain enough extra sequence to effect translation or transcription, as necessary. For a peptide library, the candidate nucleic acid generally contains cloning sites which are placed to allow in frame expression of the randomized peptides, and any fusion partners, if present, such as presentation structures. For example, when presentation structures are used, the presentation structure will generally contain the initating ATG, as a part of the parent vector. For a RNA library, the candidate nucleic acids are generally constructed with an internal CMV promoter, tRNA promoter or cell specific promoter designed for immediate and appropriate expression of the RNA structure at the initiation site of RNA synthesis. The RNA is expressed anti-sense to the direction of retroviral synthesis and is terminated as known, for example with an orientation specific terminator sequence. Interference from upstream transcription is alleviated in the target cell with the self-inactivation deletion, a common feature of certain retroviral expression systems.

Generally, the candidate nucleic acids are expressed within the cells to produce expression products of the candidate nucleic acids. As outlined above, the expression products include translation products, i.e. peptides, or transcription products, i.e. nucleic acid. The candidate bioactive agents and candidate nucleic acids are randomized, either fully randomized or they are biased in their randomization, e.g. in nucleotide/residue frequency generally or per position. By "randomized" or grammatical equivalents herein is meant that each nucleic acid and peptide consists of essentially random nucleotides and amino acids, respectively. As is more fully described below, the candidate nucleic acids which give rise to the candidate expression products are chemically synthesized, and thus may incorporate any nucleotide at any position. Thus, when the candidate nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized candidate nucleic acids.

The library should provide a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is necessary for completion of the signaling pathway. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as proposed here for expression in retroviruses, has the potential to code for $20^7$ ($10^9$) to $20^{20}$. Thus, with libraries of $10^7$ to $10^8$ per ml of retroviral particles the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different expression products are simultaneously analyzed in the subject methods. Preferred methods maximize library size and diversity.

It is important to understand that in any library system encoded by oligonucleotide synthesis one cannot have complete control over the codons that will eventually be incorporated into the peptide structure. This is especially true in the case of codons encoding stop signals (TAA, TGA, TAG). In a synthesis with NNN as the random region, there is a 3/64, or 4.69%, chance that the codon will be a stop codon. Thus, in a peptide of 10 residues, there is an unacceptable high likelihood that 46.7% of the peptides will prematurely terminate. For free peptide structures this is perhaps not a problem. But for larger structures, such as those envisioned here, such termination will lead to sterile peptide expression. To alleviate this, random residues are encoded as NNK, where K=T or G. This allows for encoding of all potential amino acids (changing their relative representation slightly), but importantly preventing the encoding of two stop residues TAA and TGA. Thus, libraries encoding a 10 amino acid peptide will have a 15.6% chance to terminate prematurely. For candidate nucleic acids which are not designed to result in peptide expression products, this is not necessary.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate bioactive agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

Thus, a number of molecules or protein domains are suitable as starting points for the generation of biased randomized candidate bioactive agents. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, biased SH-3 domain-binding oligonucleotides/peptides are made. SH-3 domains have been shown to recognize short target motifs (SH-3 domain-binding peptides), about ten to twelve residues in a linear sequence, that can be encoded as short peptides with high affinity for the target SH-3 domain. Consensus sequences for SH-3 domain binding proteins have been proposed. Thus, in a preferred embodiment, oligos/peptides are made with the following biases 1. XXXPPXPXX (SEQ ID NO:47), wherein X is a randomized residue.

2. (within the positions of residue positions 11 to −2):

```
                                           (SEQ ID NO:49)
         11   10    9    8    7    6    5    4    3    2
Met Gly aa11 aa10 aa9  aa8  aa7  Arg  Pro  Leu  Pro  Pro 1    0   -1   -2
hyd Pro hyd hyd Gly Gly Pro Pro STOP (SEQ ID NO:48)
atg ggc nnk nnk nnk nnk nnk aga cct ctg cct cca sbk ggg sbk sbk gga ggc cca cct TAA1.
```

In this embodiment, the N-terminus flanking region is suggested to have the greatest effects on binding affinity and is therefore entirely randomized. "Hyd" indicates a bias toward a hydrophobic residue, i.e.—Val, Ala, Gly, Leu, Pro, Arg. To encode a hydrophobically biased residue, "sbk" codon biased structure is used. Examination of the codons within the genetic code will ensure this encodes generally hydrophobic residues. s=g,c; b=t, g, c; v=a, g, c; m=a, c; k=t, g; n=a, t, g, c.

The candidate nucleic acids are introduced into the cells to screen for transdominant bioactive agents capable of altering the phenotype of a cell. By "introduced into " or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, LIPOFECTIN®, electroporation, viral infection, etc. The candidate nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

In a preferred embodiment, the candidate nucleic acids are part of a retroviral particle which infects the cells. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

In a preferred embodiment, the candidate nucleic acids are introduced into the cells using retroviral vectors. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins—gag, pol, and env—that are required for packaging, processing, reverse transcription, and integration of recombinant genomes. Those RNA molecules that have in cis the ψ packaging signal are packaged into maturing virions. Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al., supra: Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); and WO 94/19478; and references cited therein, all of which are incorporated by reference.

In one embodiment of the invention, the library is generated in a retrovirus DNA construct backbone, as is generally described in the examples. Standard oligonucleotide synthesis is done to generate the random portion of the candidate bioactive agent, using techniques well known in the art (see Eckstein, Oligonucleotides and Analogues, A Practical Approach, IRL Press at Oxford University Press, 1991); libraries may be commercially purchased. Libraries with up to $10^9$ unique sequences can be readily generated in such DNA backbones. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in the examples. A general schematic of the retroviral construct is depicted in FIG. 4.

The retroviruses may include inducible and constitutive promoters. For example, there are situations wherein it is necessary to induce peptide expression only during certain phases of the selection process. For instance, a scheme to provide pro-inflammatory cytokines in certain instances must include induced expression of the peptides. This is because there is some expectation that over-expressed pro-inflammatory drugs might in the long-term be detrimental to cell growth. Accordingly, constitutive expression is undesirable, and the peptide is only turned on during that phase of the selection process when the phenotype is required, and then shut the peptide down by turning off the retroviral expression to confirm the effect or ensure long-term survival of the producer cells. A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been diesgned incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In this manner the primers create a library of fragments, each containing a different random nucleotide sequence that may encode a different peptide. The ligation products are then transformed into bacteria, such as *E. coli*, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference.

Preferred systems include PhiNX-eco and PhiNX-ampho or similar cell lines, which are two cells lines as follows. The cell lines are based on the BING and BOSC23 cell lines described in WO 94/19478, which are based on the 293T cell line (a human embryonic kidney line transformed with adenovirus E1a and carrying a temperature sensitive T antigen co-selected with neomycin). The unique feature of this cell line is that it is highly transfectable with either calcium phosphate mediated transfection or lipid-based transfection protocols—greater than 50% of 293T cells can be transiently transfected with plasmid DNA. Thus, the cell line could be a cellular milieu in which retroviral structural proteins and genomic viral RNA could brought together rapidly for creation of helper-defective virus. 293T cells were therefore engineered with stably integrated defective constructs capable of producing gag-pol, and envelope protein for either ecotropic or amphotropic viruses. These lines were called BOSC23 and Bing, respectively. The utility of these lines was that one could produce small amounts of recombinant virus transiently for use in small-scale experimentation. The lines offered advantages over previous stable systems in that virus could be produced in days rather than months.

Two problems became apparent with these first generation lines over the two years they have been in wide use. First, gag-pol and envelope expression was unstable and the lines required vigilant checking for retroviral production capacity; second the structure of the vectors used for protein production were not considered fully "safe" for helper virus production; and third, one of the lines was shown to be inadvertently carrying a hygromycin-containing retrovirus. Although the BING and BOSC23 lines are useful in the present invention, all of these potentially problematic issues are addressed in the PhiNX second-generation lines. These lines are based on 293T cells as well, with the following improvements. First, the ability to monitor gag-pol production on a cell-by cell basis was made by introducing an IRES-CD8 surface marker expression cassette downstream of the reading frame of the gag-pol construct (other surface markers besides CD8 are also useful). IRES (internal ribosome entry site) sequences allow secondary or tertiary protein translation from a single mRNA transcript. Thus, CD8 expression is a direct reflection of intracellular gag-pol and the stability of the producer cell population's ability to produce gag-pol can be readily monitored by flow cytometry. Second, for both the gag-pol and envelope constructs non-Moloney promoters were used to minimize recombination potential with introduced retroviral constructs, and different promoters for gag-pol and envelope were used to minimize their inter-recombination potential. The promoters used were CMV and RSV. Two cell lines were created, PHEONIX-ECO and PHEONIX-AMPHO. Gag-pol was introduced with hygromycin as the co-selectable marker and the envelope proteins were introduced with diptheria resistance as the co-selectable marker. Finally, the cells were screened to find a relatively rare cell type that produced gag-pol and env in a uniform distribution, although this is not required. In addition, a line termed PHEONIX-gp has been produced that expresses only gag-pol. This line is available for further pseudotyping of retroviral virions with other envelope proteins such as gibbon ape leukemia virus envelope or Vesicular Stomatitus VSV-G protein, Xenotropic, or retargeting envelopes can also be added.

Both PHEONIX-ECO and PHEONIX-AMPHO were tested for helper virus production and established as being helper-virus free. Both lines can carry episomes for the creation of stable cell lines which can be used to produce retrovirus. Both lines are readily testable by flow cytometry for stability of gag-pol (CD8) and envelope expression; after several months of testing the lines appear stable, and do not demonstrate loss of titre as did the first-generation lines BOSC23 and Bing (partly due to the choice of promoters driving expression of gag-pol and envelope). Both lines can also be used to transiently produce virus in a few days. Thus, these new lines are fully compatible with transient, episomal stable, and library generation for retroviral gene transfer experiments. Finally, the titres produced by these lines have been tested. Using standard polybrene-enhanced retroviral infection, titres approaching or above $10^7$ per ml were observed for both PHEONIX-eco and PHEONIX-ampho when carrying episomal constructs. When transiently produced virus is made, titres are usually ½ to ⅓ that value.

These lines are helper-virus free, carry episomes for long-term stable production of retrovirus, stably produce gag-pol and env, and do not demonstrate loss of viral titre over time. In additon, PhiNX-eco and PhiNX-ampho are capable of producing titres approaching or above $10^7$ per ml when carrying episomal constructs, which, with concentration of virus, can be enhanced to $10^8$ to $10^9$ per ml.

In a preferred embodiment, the cell lines disclosed above, and the other methods for producing retrovirus, are useful for production of virus by transient transfection. The virus can either be used directly or be used to infect another retroviral producer cell line for "expansion" of the library.

Concentration of virus may be done as follows. Generally, retroviruses are titred by applying retrovirus-containing supernatant onto indicator cells, such as NIH3T3 cells, and then measuring the percentage of cells expressing phenotypic consequences of infection. The concentration of the virus is determined by multipying the percentage of cells infected by the dilution factor involved, and taking into account the number of target cells available to obtain a relative titre. If the retrovirus contains a reporter gene, such as lacZ, then infection, integration, and expression of the recombinant virus is measured by histological staining for lacZ exprssion or by flow cytometry (FACS). In general, retroviral titres generated from even the best of the producer cells do not exceed $10^7$ per ml, unless concentration by relatively expensive or exotic apparatus. However, as it has been recently postulated that since a particle as large as a retrovirus will not move very far by brownian motion in liquid, fluid dynamics predicts that much of the virus never comes in contact with the cells to initiate the infection process. However, if cells are grown or placed on a porous filter and retrovirus is allowed to move past cells by gradual gravitometric flow, a high concentration of virus around cells can be effectively maintained at all times. Thus, up to a ten-fold higher infectivity by infecting cells on a porous membrane and allowing retrovirus supernatant to flow past them has been seen. This should allow titres of $10^9$ after concentration.

The candidate nucleic acids, as part of the retroviral construct, are introduced into the cells to screen for trans-dominant bioactive agents capable of altering the phenotype of a cell.

As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive agent. As is more fully described below, cell types implicated in a wide variety of disease conditions are particularly useful, so long as a suitable screen may be designed to allow the selection of cells that exhibit an altered phenotype as a consequence of the presence of a transdominant bioactive agent within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be genetically engineered, that is, contain exogeneous nucleic acid, for example, to contain target molecules.

In a preferred embodiment, a first plurality of cells is screened. That is, the cells into which the candidate nucleic acids are introduced are screened for an altered phenotype. Thus, in this embodiment, the effect of the transdominant bioactive agent is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the retroviral molecular library, i.e. a different candidate nucleic acid, although as will be appreciated by those in the art, some cells within the library may not contain a retrovirus, and some may contain more than one. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, etc.

In a preferred embodiment, the candidate nucleic acids are introduced into a first plurality of cells, and the effect of the candidate bioactive agents is screened in a second or third plurality of cells, different from the first plurality of cells, i.e. generally a different cell type. That is, the effect of the transdominant bioactive agents is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the candidate nucleic acids (for example, when inducible promoters are used), to produce the candidate expression products, either translation or transcription products.

Thus, the methods of the present invention comprise introducing a molecular library of randomized candidate nucleic acids into a plurality of cells, a cellular library. Each of the nucleic acids comprises a different, generally randomized, nucleotide sequence. The plurality of cells is then screened, as is more fully outlined below, for a cell exhibiting an altered phenotype. The altered phenotype is due to the presence of a transdominant bioactive agent.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive agent can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the randomized nucleic acid was introduced; in other embodiments, the altered phenotype is detected in a second cell which is responding to some molecular signal from the first cell.

An altered phenotype of a cell indicates the presence of a transdominant bioactive agent. By "transdominant" herein is meant that the bioactive agent indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable target; that is, not an effect upon the encoded entity itself. As such, transdominant effects include many well-known effects by pharmacologic agents upon target molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide is the ability to inhibit NF-κB signaling by binding to IκB-α at a region critical for its function, such that in the presence of sufficient amounts of the peptide (or molecular entity), the signaling pathways that normally lead to the activation of NF-κB through phosphorylation and/or degradation of IκB-α are inhibited from acting at IκB-α because of the binding of the peptide or molecular entity. In another instance, signaling pathways that are normally activated to secrete IgE are inhibited in the presence of peptide. Or, signaling pathways in adipose tissue cells, normally quiescent, are activated to metabolize fat. Or, in the presence of a peptide, intracellular mechanisms for the replication of certain viruses, such as HIV-I, or Herpes viridae family members, or Respiratory Syncytia Virus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent, independent of the β-lactamase, that bound to the β-lactamase in such a way that it enhanced or diminished the function of the β-lactamase by virtue of its binding to β-lactamase.

In general, cis-effects are effects within molecules wherein elements that are interacting are covalently joined to each other although these elements might individually manifest themselves as separable domains. Trans-effects (transdominant in that under some cellular conditions the desired effect is manifested) are those effects between distinct molecular entities, such that molecular entity A, not covalently linked to molecular entity B, binds to or otherwise has an effect upon the activities of entity B. As such, most known pharmacological agents are transdominant effectors.

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the candidate nucleic acid and/or the bioactive agent is isolated from the positive cell. This may be done in a number of ways. In a preferred embodiment, primers complementary to DNA regions common to the retroviral constructs, or to specific components of the library such as a rescue sequence, defined above, are used to "rescue" the unique random sequence. Alternatively, the bioactive agent is isolated using a rescue sequence. Thus, for example, rescue sequences comprising epitope tags or purification sequences may be used to pull out the bioactive agent, using immunoprecipitation or affinity columns. In some instances, as is outlined below, this may also pull out the primary target molecule, if there is a sufficiently strong binding interaction between the bioactive agent and the target molecule. Alternatively, the peptide may be detected using mass spectroscopy.

Once rescued, the sequence of the bioactive agent and/or bioactive nucleic acid is determined. This information can then be used in a number of ways.

In a preferred embodiment, the bioactive agent is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of a bioactive agent is used to generate more candidate bioactive agents. For example, the sequence of the bioactive agent may be the basis of a second round of (biased) randomization, to develop bioactive agents with increased or altered activities. Alternatively, the second round of randomization may change the affinity of the bioactive agent. Furthermore, it may be desirable to put the identified random region of the bioactive agent into other presentation structures, or to alter the sequence of the constant region of the presentation structure, to alter the conformation/shape of the bioactive agent. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive agent or the bioactive nucleic acid encoding it is used to identify target molecules, i.e. the molecules with which the bioactive agent interacts. As will be appreciated by those in the art, there may be primary target molecules, to which the bioactive agent binds or acts upon directly, and there may be secondary target molecules, which are part of the signalling pathway affected by the bioactive agent; these might be termed "validated targets".

In a preferred embodiment, the bioactive agent is used to pull out target molecules. For example, as outlined herein, if the target molecules are proteins, the use of epitope tags or purification sequences can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide bioactive agent and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon. Once primary target molecules have been identified, secondary target molecules may be identified in the same manner, using the primary target as the "bait". In this manner, signalling pathways may be elucidated. Similarly, bioactive agents specific for secondary target molecules may also be discovered, to allow a number of bioactive agents to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive agent is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, random libraries can be introduced into any tumor cell (primary or cultured), and peptides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then random libraries introduced into these cells, to select for bioactive agents which reverse or correct the transformed state. One of the signal features of oncogene transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive agent will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive agents capable of blocking the ability of the growth factor or cytokine to stimulate the tumor cell. The introduction of random libraries into specific tumor cells with the addition of the growth factor or cytokine, followed by selection of bioactive agents which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have random libraries introduced into them, and peptides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular peptide activators of this gene could block metastasis, and a screen for its upregulation (by fusing it to a reporter gene) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Peptides which act intracellularly to block the release of combinations of proteases required for invasion, such as the matrix metalloproteases and urokinase, could also be effective antimetastatics.

In a preferred embodiment, the random libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a peptide or small molecule derived from a peptide could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening of bioactive agents which restore the constitutive function of the brca-1 or brca-2 genes, and other tumor suppressor genes important in breast cancer such as the adenomatous polyposis coli gene (APC) and the Drosophila discs-large gene (Dlg), which are components of cell—cell junctions. Mutations of brca-1 are important in hereditary ovarian and breast cancers, and constitute an additional application of the present invention.

In a preferred embodiment, the methods of the present invention are used to create novel cell lines from cancers from patients. A retrovirally delivered short peptide which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Ebstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing nucleic acids encoding peptides which inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive agents are inserted into cardiomyocytes, the cells are subjected to the insult, and bioactive agents are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the candidate nucleic acids encoding candidate bioactive agents, followed by the application of arrythmogenic insults, with screening for bioactive agents that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive agents which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias. Bioactive agents are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive agents which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for peptides that either: 1) downregulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Bioactive agents can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Candidate bioactive agent libraries can be inserted into these cell types and their proliferation in response to specific stimuli monitored. One application may be intracellular peptides which block the expression or function of c-myc and other oncogenes in smooth muscle cells to stop their proliferation. A second application may involve the expression of libraries in vascular smooth muscle cells to selectively induce their apoptosis. Application of small molecules derived from these peptides may require targeted drug delivery; this is available with stents, hydrogel coatings, and infusion-based catheter systems. Peptides which downregulate endothelin-1A receptors or which block the release of the potent vasoconstrictor and vascular smooth muscle cell mitogen endothelin-1 may also be candidates for therapeutics. Peptides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive agent libraries can be inserted into capillary endothelial cells and their growth monitored. Stimuli such as low oxygen tension and varying degrees of angiogenic factors can regulate the responses, and peptides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find peptides that regulate LDL and HDL metabolism. Candidate libraries can be inserted into the appropriate cells (including hepatocytes, mononuclear leukocytes, endothelial cells) and peptides selected which lead to a decreased release of LDL or diminished synthesis of LDL, or conversely to an increased release of HDL or enhanced synthesis of HDL. Bioactive agents can also be isolated from candidate libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive agents that regulate or inhibit the responses of neuropeptide Y (NPY), cholecystokinin and galanin receptors, are particularly desirable. Candidate libraries can be inserted into cells that have these receptors cloned into them, and inhibitory peptides selected that are secreted in an autocrine manner that block the signaling responses to galanin and NPY. In a similar manner, peptides can be found that regulate the leptin receptor.

In a preferred embodiment, the present methods are useful in neurobiology applications. Candidate libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting candidate libraries into these cells, and then looking for bioactive agents that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, candidate libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Candidate libraries can be inserted into cells removed from active psoriatic plaques, and bioactive agents isolated which decrease the rate of growth of these cells.

In a preferred embodiment, the present methods are useful in the regulation or inhibition of keloid formation (i.e. excessive scarring). Candidate libraries inserted into skin connective tissue cells isolated from individuals with this condition, and bioactive agents isolated that decrease proliferation, collagen formation, or proline incorporation. Results from this work can be extended to treat the excessive scarring that also occurs in burn patients. If a common peptide motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate libraries can be inserted into skin connective tissue cells, and bioactive agents isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate libraries can be inserted into melanocytes and known stimuli that increase the synthesis of melanin applied to the cells. Bioactive agents can be isolated that inhibit the synthesis of melanin under these conditions.

In a preferred embodiment, the present methods are useful in endocrinology applications. The retroviral peptide library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1–17, mimetics) or inhibits its action by either blocking the release of the hormone, blocking its binding to a specific receptor or carrier protein (for example, CRF binding protein), or inhibiting the intracellular responses of the specific target cells to that hormone. Selection of peptides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive agents isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. The extracellular anchored constructs offer superb tools for such a discovery. Into the transmembrane, epitope tagged, glycine-serine tethered constructs (ssTM V G20 E TM), one can place a random, cyclized peptide library of the general sequence CNNNNNNNNNNC or C-$(X)_n$-C (SEQ ID NO:50). Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry.

Viruses are known to enter cells using specific receptors to bind to cells (for example, HIV uses CD4, coronavirus uses CD13, murine leukemia virus uses transport protein, and measles virus uses CD44) and to fuse with cells (HIV uses chemokine receptor). Candidate libraries can be inserted into target cells known to be permissive to these viruses, and bioactive agents isolated which block the ability of these viruses to bind and fuse with specific target cells.

In a preferred embodiment, the present invention finds use with infectious organisms. Intracellular organisms such as mycobacteria, listeria, salmonella, pneumocystis, yersinia, leishmania, T. cruzi, can persist and replicate within cells, and become active in immunosuppressed patients. There are currently drugs on the market and in development which are either only partially effective or ineffective against these organisms. Candidate libraries can be inserted into specific cells infected with these organisms (pre- or post-infection), and bioactive agents selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive agents can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Candidate libraries can be introduced into the specific cell types where specific changes leading to cellular damage or apoptosis by the antibiotics are produced, and bioactive agents can be isolated that confer protection, when these cells are treated with these specific antibiotics.

Furthermore, the present invention finds use in screening for bioactive agents that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be inserted into specific cells derived from kidney cells and cells of the choroid plexus known to have active transport mechanisms for antibiotics. Bioactive agents can then be isolated which block the active transport of specific antibiotics and thus extend the serum halflife of these drugs.

In a preferred embodiment, the present methods are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Candidate libraries can be introduced into specific cell types with characteristic drug-induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Candidate libraries can be introduced into liver or kidney cells following the exposure of these cells to the drug known to produce the toxic metabolite. Bioactive agents can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate libraries can be introduced into tumor cell lines (primary and cultured) that have demonstrated specific or multiple drug resistance. Bioactive agents can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Candidate libraries are particularly suited to screening for peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for peptide inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of candidate libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate libraries can be inserted into B cells and bioactive agents selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and ILI-17, may be selected, or agents that bind cytokines such as TNF-$\alpha$, before they bind their receptor.

Antigen processing by mononuclear leukocytes (ML) is an important early step in the immune system's ability to recognize and eliminate foreign proteins. Candidate agents can be inserted into ML cell lines and agents selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive agents selected which inhibit the synthesis, release and binding to the cognate receptor of each of these types of mediators.

In a preferred embodiment, the present methods are useful in biotechnology applications. Candidate library expression in mammalian cells can also be considered for other pharmaceutical-related applications, such as modification of protein expression, protein folding, or protein secretion. One such example would be in commercial production of protein pharmaceuticals in CHO or other cells. Candidate libraries resulting in bioactive agents which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Random peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive agent sequence identified can then be coupled to an antibody, enzyme, drug, imaging agent or substance for which organ targeting is desired. Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a random peptide to a protein binding region to allow interactions with molecules sterically close, i.e. within a signalling pathway, to localize the effects to a functional area of interest.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Proof of Concept Experiments

A number of systems were used to prove that the retroviral constructs outlined herein were able to result in a selectable phenotype.

Bcl2 and CPP32 Protection from apoptosis

It is known that Bcl2 and the CPP32 peptide is able to inhibit apoptosis induced by tumor necrosis factor and cycloheximide.

Apotag assay: TUNEL (TdT-mediated dUTP-fluorescein nick end labeling) Boehringer Mannheim kit, catalog No. 168795

3T3 cells transiently infected with either MFGLacZ, BCL2, or CPP322 plasmids were grown to 50% confluence at the time of induction with hTNFa (50 ng/ml media) and cycloheximide (100 mg/ml media) for 6 hours. Cells were washed at 6 hours and harvested at 24 hours after induction. Cells were harvested by pooling all media from cells (in order to collect any apoptotic, floating cells) with the washings and trypsinized cells. The cells were spun and washed with PBS containing 1% BSA, transferred to an eppendorf tube and the wash repeated once. Cells were fixed in 4% paraformaldehyde at room temperature for 30 minutes, washed in PBS/BSA, then resuspended in permeabilisation buffer for 2 minutes on ice. After permeabilisation, cells were washed twice in PBS/BSA and incubated at 37° C. for 1 hour with labeling buffer containing fluoresceinated dUTP, unlabeled nucleotide mixture and terminal deoxynucleotidyl transferase (TdT). Cells were washed twice with PBS/BSA, resuspended in PBS/BSA and transferred to a FACS tube for analysis. Samples were also visualized under the fluorescence microscope. The results showed that expression of Bcl2 or the CPP32 peptide in 3T3 cells from an MSCV retroviral promoter in vivo was able to inhibit apoptosis induced by tumor necrosis factor and cycloheximide.

Propidium Iodide staining of fixed cells to assay for apoptosis: (Sherwood and Schimke, Methods in Cell Biology, 46:77–87, 1995)

3T3 cells transiently infected with MFGLacZ, Bcl2, or CPP32 were plated and treated with TNF/CXH as described above, and harvested and washed as above. Cells were then resuspended in 70% ethanol in PBS at 4oC and kept at 4oC overnight. When ready to FACS, cells were stained with propidium iodide as follows. Cells were spun at 14,000 RPM for 10 seconds and washed once with PBS/BSA. Cells were then resuspended in 50 ml staining solution (PBS with 50 mg/ml RNase A (DNase-free) with 10 mg/ml propidium iodide) and incubated at 37° C. for at least 1 hour. Cells were then pelleted and resuspended in PBS/BSA solution containing 10 mg/ml propidium iodide and analyzed by FACS scanning. The results showed that expression of BCL2 or CPP32 peptide in 3T3 cells was able to inhibit apoptosis induced by tumor necrosis factor and cycloheximide as measure by PI staining of cells, extending our previous results.

Ethidium Bromide/Acridine Orange Staining of BAF3 Cells to Study Cell Morphology BAF3 cells were infected with WZL IRES NEO retroviral vectors containing no insert (WIN) or DNA coding for LacZ (ZIN), Bcl2 (BIN), CPP32 peptide (CIN), or scrambled peptide control (PIN). Cells were selected in G418 after infection with above retroviral vectors and survivors were stimulated with 5 mg/ml FAS antibody. After stimulation, cells were stained with ethidium bromide and acridine orange (2 mg/ml each) and visualized under the fluorescence microscope using the ultraviolet filter. 250 cells were counted and the percent of cells which were apoptotic were calculated. Similar to results obtained in 3T3 cells stimulated with TNF/CXH, the CPP32 encoding vectors are able to inhibit FAS induced apoptosis. The peptide control also had an effect in this system approximately half of that seen with BCL2 or the CPP32 peptide.

Enzymatic Assay of CPP32 activity

CPP32 Assay Kit: Clontech CPP32 Colorimetric Assay Kit (Cat. No. K2027-2): 3T3 cells were infected with the vectors described in Part I, section C, and selected in G418 media prior to assay. 6-well plates of 3T3 cells at near confluence were stimulated with TNF/CXH as described above and harvested at 30 min, 1, 2 and 4 hours after stimulation as follows. Cells were trypsinized and collected as described above. After transfering to an eppendorf tube, cells were spun and resuspended in 50 ml chilled Cell Lysis Buffer. Cells were incubated for 10 minutes on ice, then 50 ml of 2×Reaction Buffer containing DTT was added to each tube. 5 ml of the colorimetric conjugated substrate (DEVD-paranitroanilide, 50 mM final concentration) was added to each tube and incubated at 37° C. for 30 minutes. Samples were transferred to a 96 well plate and read on a spectrophotometer at O.D. of 405. The results showed that cell extracts from WIN cells have increased CPP32 enzyme activity at 2 hours as measured by cleavage of DEVD-pNA substrate to its colorometrically detectable form pNA. By 4 hours, cells have begun to die and the activity is decreased. In cells containing BCL2 or the CPP32 peptide inhibitor, this rise in activity is not seen. In the case of BCL2, it should be due to inhibition of apoptosis upstream of the enzyme. With CPP32 inhibitor peptide, it should be due to direct inhibition of enzymatic activity. These in vitro results are consistent with the results seen in cell death assays described above.

Localization studies using PKC inhibitor

Murine 10T1/2 Clone 8 cells were stimulated with PMA which is known to cause translocation of PKC from the cytoplasm to the nucleus. This translocation is thought to be mediated through binding to a protein at the site of action, termed a RAC (receptor for activated protein kinase C) protein. Uninfected clone 8 cells were compared to cells infected with pBabe puro retroviral constructs containing sequences coding for either Flu-epitope (MGGGYPYDVPDYAGSLZ; SEQ ID NO:51) tagged scrambled peptide control or inhibitor peptide (GKQKTKTIKGPP; SEQ ID NO:52) which is identical to the C2 region of all the PKC isozymes. We then assayed the cells by immunohistochemistry using an antibody specific for PKCa and visualized with a secondary antibody conjugated to horseradish peroxidase.

This experiment was done at two different cell densities as follows:

1. Cells were plated at 2,000 cells/cm² onto 22 mm square polylysine coated coverslips and allowed to grow for 2 days. On 3/20, cells were nearly confluent. Cells were replated at a lower density and assayed with identical conditions on 3/27.

2. PMA was added at $10^{-5}$M to the media for 30 minutes at 37° C.

3. Cells were rinsed with SCB buffer (physiologic buffer prewarmed to 37° C. before use) and then placed into 3.7% glutaraldehyde in SCB buffer for 20 minutes at 37° C.

4. Cells were then washed in SCB buffer then incubated with SCBT (SCB containing 0.1% Triton X-100) for 10 minutes at room temperature.

5. Coverslips were removed from the 6-well plate and dip washed in 0.1% tween/PBS at room temperature and placed onto parafilm in a covered container.

6. Coverslips were incubated with 1.5% goat blocking serum in PBS with agitation in a humidified environment at room temperature.

7. Solutions were aspirated off the coverslip and coverslips were then washed with PBS. Primary anti-PKCa antibody was placed onto coverslips and incubated for 30 minutes at room temperature as above. A 1:500 dilution of anitbody was used in all experiments.

8. Coverslips were then washed with PBS three times and then incubated for 30 minutes at room temperature with biotin-conjugated second step antibody as provided in Santa Cruz ABC ImmunoStain Sytems kit. Coverslips were then washed three times with PBS.

9. Coverslips were then incubated in avidin biotin enzyme reagent (as supplied with kit) for 30 minutes at room temperature. Coverslips were then washed for 10 minutes in PBS after being placed back into 6-well plates.

10. Coverslips were rinsed with 0.5% Triton X-100/PBS for 30 seconds and incubated in DAB solution for 5 minutes. Reaction was stopped by addition of distilled water to well.

11. Coverslips were then dehydrated through alcohols and xylene and mounted onto slides with Permount and visualised and photographed by light microscopy.

The result showed that basically, control clone 8 cells showed predominantly cytoplasmic and perinuclear staining, while PMA induced cells consistently showed translocation to the nucleus. Cells infected with constructs coding for the scrambled peptide showed similar staining. Cells infected with constructs coding for peptides identical to the C2 region of PKC showed predominantly cytoplasmic and perinuclear staining in both control and PMA induced cells suggesting that this peptide is able to specifically inhibit translocation of activated PKCa to its RAC protein upon stimulation of the cells with PMA. It is also possible using similarly infected cells to see the downstream results of peptide expression upon gene activity. Cells were infected with retroviruses expressing either the PKCb2.1, PKC2.1 peptide, a dominant negative ras protein control, combinations of these viruses, or no virus at all. Cells were stimulated with PMA at 100 ng/ml, PDGF-M, or PDGF-BB. mRNA was prepared and northern blots were performed for fos gene expression (induced by PKC activation) or the ribosomal protein P0, a loading control mRNA whose expression is not known to be acted upon by signaling systems induced by PKC. The PKC peptides can markedly reduce expression of the fos gene mRNA. Indeed, an unexpected result was that under certain conditions there is activation of the mRNA expression. This latter results confirms that novel outcomes can occur upon expression of peptides within cells.

Example 2 pBabe Puro Retroviral Libraries and Apoptosis

A series of retroviral constructs have been designed for expression of randomized and biased peptides within target cell populations. The peptide is expressed from a retroviral promoter. The translation unit has several important components. Glycine following the initiator methionine at the amino terminus stabilizes the peptide and enhances cytoplasmic half-life, according to Varshavsky's N-End Rule. In some constructs, a nine amino acid flu epitope tag has been incorporated to permit co-precipitation of the rare peptide and any molecule to which it has affinity, by using monoclonal antibodies to the epitope. Glycines are encoded before and after the random/biased expression product encoding regions to provide some molecular flexibility. Two carboxyl-terminal prolines are encoded to confer stability to carboxypeptidase.

For construction of a large library two primers were made (schematized in FIG. 1). The first, designated the random peptide primer, consists of 1) a complementary region for vector priming, 2) the regions mentioned above, and 3) a random or biased expression product region, were presented as a 30 base sequence encoding a peptide of length 10 amino acids. In addition, we have inserted a stop codon in all three reading frames in case of minor deletions or insertions in the random region. The design of the primer ensures a glycine/proline termination in most reading frames. The second primer is downstream in the vector and primes a region of the plasmid that contains a unique Not I site. These primers are used to create a library of fragments, each containing a different nucleotide sequence that each potentially encodes a different peptide. These families of fragments are ligated to vector fragments containing puromycin selection sequence, a 3'LTR, and a bacterial origin of replication. The ligation products are then electroporated into E. coli and DNA is prepared from the resulting library. Using this technique, we have constructed independent random libraries with up to $2 \times 10^8$ unique inserts. Sequencing multiple individual inserts demonstrates they have the structure as defined by Primer 1, and the peptides encoded are random. Such libraries thus made contain subsets of the total $10^{13}$ predicted peptides.

Generation of Retroviral Peptide Libraries

A scheme for generating a peptide library in the pBabe Puro vector is shown in FIG. 2. Primers for PCR were synthesized, purified and deprotected according to standard protocols. Primer 1, complementary to polylinker sequences in the pBabe Puro retroviral construct, has the sequence 5' GCT TAG CAA GAT CTC TAC GGT GGA CCK NNK NNK NNK NNK NNK NNK NNK NNK NNC CCC ACT CCC ATG GTC CTA CGT ACC ACA CTG GG 3' (SEQ ID NO:53). N represents any of the four bases; K is limited to G or T. Primer 2 has the sequence 5' GCT TAG CAA GAT CTG TGT GTC AGT TAG GGT GTG G 3' (SEQ ID NO:54) and is complementary to sequences within the pUC18 origin of replication. PCR was carried out for 8 rounds using primer 1, primer 2, Babe Puro as template, and a mixture of Taq DNA Polymerase (Promega) and Deep Vent DNA Polymerase (New England Biolabs) in a ratio of 128 Taq: 1 Deep Vent as described in Barnes (1994) Proc. Natl. Acad. Sci. USA, 91, pp. 2216–2220. The amplified PCR product was purified, digested with restriction enzymes Bgl II and Not I (Promega), purified again and ligated with the corresponding Bam HI-Not I fragment of pBabe Puro. After transformation the resulting library contained ~$2 \times 10^8$ clones, greater than 80% of which contained inserts.

PMSCV-PC and pBabeMN-PC retroviral construct libraries

Oligonucleotides were synthesized and purified according to standard protocols. The "library" oligonucleotides have the sequence 5' CTG GAG MAA CAG GAC CAT GGG C (NNK)10 GGG CCC CCT TAA ACC ATT AAA T 3' (SEQ ID NO:55) or 5' CTG GAG MAA CAG GAC CAT GGG CNN KNN KNN KCC TCC CNN KCC TNN KNN KGG GCC CCC TTA MAA CAT TAA AT 3' (SEQ ID NO:56). A third oligonucleotide ("constant"), complementary to the 3' ends of the library oligonucleotides, has the sequence 5'TCA TGC ATC CAA TTT AAT GGT TTA AG 3' (SEQ ID NO:57). As shown in FIG. 2, each library oligonucleotide is annealed to the constant oligonucleotide, converted to double stranded DNA with Sequenase (United States Biochemical) or Kienow (Promega), digested with restriction enzyme Bst XI (New England Biolabs), and purified and ligated with the appropriate Bst XI-digested retroviral construct. Transformation efficiencies are ~$2 \times 10^8$ clones per microgram of ligated DNA, greater than 90% of which contain an insert. A representative retrovirus is shown in FIG. 4; see also, retroviral nucleotide sequence below:

Retroviral vector with presentation construct.

(SEQ ID NO:58)

```
TGAAAGACCCCACCTGTAGGTTTGGCAAGCTAGCTTAAGTAACGCCATTTTGCAAGGCATGGAAA

ATACATAACTGAGAATAGAGAAGTTCAGATCAAGGTTAGGAACAGAGAGACAGCAGAATATGGG

CCAAACAGGATATCTGTGGTAAGCAGTTCCTGCCCCGGCTCAGGGCCAAGAACAGATGGTCCCC

AGATGCGGTCCCGCCCTCAGCAGTTTCTAGAGAACCATCAGATGTTTCCAGGGTGCCCCAAGGA

CCTGAAAATGACCCTGTGCCTTATTTGAACTAACCAATCAGTTCGCTTCTCGCTTCTGTTCGCGC

GCTTCTGCTCCCCGAGCTCAATAAAAGAGCCCACAACCCCTCACTCGGCGCGCCAGTCCTCCGA

TAGACTGCGTCGCCCGGGTACCCGTATTCCCAATAAAGCCTCTTGCTGTTTGCATCCGAATCGTG

GACTCGCTGATCCTTGGGAGGGTCTCCTCAGATTGATTGACTGCCCACCTCGGGGGTCTTTCAT

TTGGAGGTTCCACCGAGATTTGGAGACCCCTGCCTAGGGACCACCGACCCCCCGCCGGGAGG

TAAGCTGGCCAGCGGTCGTTTCCTGTCTGTCTCTGTCTTTGTGCGTGTTTGTGCCGGCATCTAAT

GTTTGCGCCTGCGTCTGTACTAGTTAGCTAACTAGCTCTGTATCTGGCGGACCCGTGGTGGAAC

TGACGAGTTCTGAACACCCGGCCGCAACCCTGGGAGACGTCCCAGGGACTTTGGGGGCCGTTT

TTGTGGCCCGACCTGAGGAAGGGAGTCGATGTGGAATCCGACCCCGTCAGGATATGTGGTTCT

GGTAGGAGACGAGAACCTAAAACAGTTCCCGCCTCCGTCTGAATTTTTGCTTTCGGTTTGGAACC

GAAGCCGCGCGTCTTGTCTGCTGCAGCGCTGCAGCATCGTTCTGTGTTCTCTCTGTCTGACTGT

GTTTCTGTATTTGTCTGAAAATTAGGGCCAGACTGTTACCACTCCCTTAAGTTTGACCTTAGGTCA

CTGGAAAGATGTCGAGCGGATCGCTCACAACCAGTCGGTAGATGTCAAGAAGAGACGTTGGGTT

ACCTTCTGCTCTGCAGAATGGCCAACCTTTAACGTCGGATGGCCGCGAGACGGCACCTTTAACC
```

-continued

```
GAGACCTCATCACCCAGGTTAAGATCAAGGTCTTTTCACCTGGCCCGCATGGACACCCAGACCA
GGTCCCCTACATCGTGACCTGGGAAGCCTTGGCTTTTGACCCCCCTCCCTGGGTCAAGCCCTTT
GTACACCCTAAGCCTCCGCCTCCTCTTCCTCCATCCGCCCCGTCTCTCCCCCTTGAACCTCCTC
GTTCGACCCCGCCTCGATCCTCCCTTTATCCAGCCCTCACTCCTTCTCTAGGCGCCGGAATTCCA
GGACCATGGGCGGGCCCCCTTAAACCATTAAATTGGTAAAATAAAGGATCCGTCGACCTGCAGC
CAAGCTTATCGATAAAATAAAAGATTTTATTTAGTCTCCAGAAAAAGGGGGGAATGAAAGACCCC
ACCTGTAGGTTTGGCAAGCTAGCTTAAGTAACGCCATTTTGCAAGGCATGGAAAATACATAACTG
AGAATAGAGAAGTTCAGATCAAGGTTAGGAACAGAGAGACAGCAGAATATGGGCCAAACAGGAT
ATCTGTGGTAAGCAGTTCCTGCCCCGGCTCAGGGCCAAGAACAGATGGTCCCCAGATGCGGTC
CCGCCCTCAGCAGTTTCTAGAGAACCATCAGATGTTTCCAGGGTGCCCCAAGGACCTGAAAATG
ACCCTGTGCCTTATTTGAACTAACCAATCAGTTCGCTTCTCGCTTCTGTTCGCGCGCTTCTGCTC
CCCGAGCTCAATAAAAGAGCCCACAACCCCTCACTCGGCGCGCCAGTCCTCCGATAGACTGCGT
CGCCCGGGTACCCGTGTATCCAATAAACCCTCTTGCAGTTGCATCCGACTTGTGGTCTCGCTGTT
CCTTGGGAGGGTCTCCTCTGAGTGATTGACTACCCGTCAGCGGGGGTCTTTCATTCGTAATCAT
GGTCATAGCTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAATCGGCCAACGCGCG
GGGAGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAAAAATCGACG
CTCAAGTCAGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGC
TACACTAGAAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGACGCT
CAGTGGAACGAAAACTCACGTTAAGGGATTTTGGTCATGAGATTATCAAAAAGGATCTTCACCTA
GATCCTTTTAAATTAAAAATGAAGTTTTAAATCAATCTAAAGTATATATGAGTAAACTTGGTCTGAC
AGTTACCAATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGG
AAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATTCTCTTACTGT
```

-continued

```
CATGCCATCCGTAAGATGCTTTTCTGTGACTGGTGAGTACTCAACCAAGTCATTCTGAGAATAGT

GTATGCGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGATCTTACCG

CTGTTGAGATCCAGTTCGATGTAACCCACTCGTGCACCCAACTGATCTTCAGCATCTTTTACTTTC

ACCAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGTTATTG

TCTCATGAGCGGATACATATTTGAATGTATTTAGAAAAATAAACAAATAGGGGTTCCGCGCACATT

TCCCCGAAAAGTGCCACCTGACGTCTAAGAAACCATTATTATCATGACATTAACCTATAAAAATAG

GCGTATCACGAGGCCCTTTCGTCTCGCGCGTTTCGGTGATGACGGTGAAAACCTCTGACACATG

CAGCTCCCGGAGACGGTCACAGCTTGTCTGTAAGCGGATGCCGGGAGCAGACAAGCCCGTCAG

GGCGCGTCAGCGGGTGTTGGCGGGTGTCGGGGCTGGCTTAACTATGCGGCATCAGAGCAGATT

GTACTGAGAGTGCACCATATGCGGTGTGAAATACCGCACAGATGCGTAAGGAGAAAATACCGCA

TCAGGCGCCATTCGCCATTCAGGCTGCGCAACTGTTGGGAAGGGCGATCGGTGCGGGCCTCTT

CGCTATTACGCCAGCTGGCGAAAGGGGGATGTGCTGCAAGGCGATTAAGTTGGGTAACGCCAG

GGTTTTCCCAGTCACGACGTTGTAAAACGACGGCCAGTGCCACGCTCTCCCTTATGCGACTCCT

GCATTAGGAAGCAGCCCAGTAGTAGGTTGAGGCCGTTGAGCACCGCCGCCGCAAGGAATGGTG

CATGCAAGGAGATGGCGCCCAACAGTCCCCCGGCCACGGGCCTGCCACCATACCCACGCCGA

AACAAGCGCTCATGAGCCCGAAGTGGCGAGCCCGATCTTCCCCATCGGTGATGTCGGCGATATA

GGCGCCAGCAACCGCACCTGTGGCGCCGGTGATGCCGGCCACGATGCGTCCGGCGTAGAG
```

Peptide Library Infection of a Factor-dependent Line and Outgrowth of an Apoptosis-Resistant Line The Baf/3 cell line is an IL-3 dependent cell that undergoes rapid apoptosis in the absence af IL-3. Thus it makes an attractive cell line for dominant effector peptides. Cells expressing a peptide that inhibits apoptosis are readily selected against the background of dying cells. We chose this cell line as a model for demonstrating peptide selection.

A retroviral library containing $5\times10^6$ independent peptide inserts was transfected into BOSC23 cells and converted into retrovirus with an approximate titer of $5\times10^5$ per ml. Twelve ml of viral supernatant was used to infect $6\times10^6$ Baf/3cells (2 ml per infection of $1\times10^6$ cells in independent infections). Cells were grown for 3 days after infection in the presence of IL-3 to allow retroviral integration and peptide expression. After three days IL-3 was withdrawn and the cells allowed to grow for two weeks. After two weeks, one well of six had outgrowth of cells that survive in the absence of IL-3, indicating the presence of an apoptosis-inhibiting peptide. Peptides derived in this manner may effect the IL-3 independence by positive dominancy (i.e., mimic or circumvent the positive regulatory role of IL-3) or by inhibition (i.e., prevent the apoptosis process upon IL-3 withdrawal).

Example 3 pMSCVpc Vector Construction and Apoptosis

The retroviral vector pMSCVpc was prepared by cloning an insert containing sequences encoding a Kozak translation initiation sequence, BstXI sites for cloning library inserts, NruI and XhoI sites and stop codons in all three reading frames, into the EcoRI and BamHI sites of pMSCV neo.

BstXI Restriction Digestion

200 µg pMSCVpc vector DNA was combined with 40 µl 10×NEBuffer 3 and 30 µl BstX I (10 units/µl) in a total volume of 400 µl. The sample was incubated overnight at 55° C., phenol extracted, and digested with XhoI, and purified on a potassium acetate step gradient using 10, 15, 20 and 25% solutions of potassium acetate. The DNA was precipitated, with a recovery of 40%.

Library Insert Preparation

Oligonucleotide Synthesis

Oligonucleotides (OL) with the following sequences were synthesized:

(SEQ ID NO:59)
OL-1: 5'-CTG GAG AAC CAG GAC C<u>AT GGG CAA GAG AAA GGG CGA TGA GGT GGA TGG AGT GGG GCC CCC TTA</u> AAC CAT TAA AT-3'

The underlined region encodes a peptide with the sequence MGKRKGDEVDGVGPP (SEQ ID NO:60). This peptide was shown to inhibit Fas-mediated and Staurosporin induced apoptosis when expressed in cells with a retrovirus.

```
                                                                   (SEQ ID NO:61)
OL-2:  5'-CTG GAG AAC CAG GAC CAT GGG CAA GAG AAA GGG CNN KNN KNN KGA KNN KGT

GGG GCC CCC TTA AAC CAT TAA AT-3'
```

Variable region: N=A,C,G,T (equimolar) K=G,T (equimolar)

Limiting the K position of each codon to G or T reduces stop codon generation and codon usage bias. The underlined region encodes a randomized peptide with the sequence MGKRKGXXXD/EXVGPP. (SEQ ID NO:62)

OL-3: 5'-TCA TGC ATC CAA TTT AAT GGT TTA AG-3' (SEQ ID NO:63)

The 15 3'-bases of OL-3 are complementary to the 15 3'-bases of OL-1 and OL-2.

OL-1 and OL-2 were synthesized at 1 $\mu$M scale, while OL-3 was synthesized at standard 40 nM scale. All of the oligos were synthesized with trityl-on, deprotected and purified on OPC columns according to the manufacturer's directions (Applied Biosystems). Each oligo was resuspended in 200 $\mu$l 10 mM Tris pH 8.5 without EDTA. The DNA concentration was determined by measuring the absorbance at 260 nm.

PCR was done with 50 pmole of either OL-1 or OL-2 and 50 pmole of OL-3. Phenol extraction and ethanol precipitation was done, and the resulting DNA was run on a 10% nondenaturing 10% acrylamide gel, with ethidium bromide staining.

The samples were quantitated, ligated, precipitated and electroporated into electrocompetent TOP10F' *E. Coli* (Invitrogen) using standard techniques (see Current Protocols in Molecular Biology, section 1.8.4). A test transformation yielded $5 \times 10^9$ transformants per $\mu$g of pUC DNA. After transformation, the transformation efficiency was determined by plating dilutions onto LB-amp plates (100 $\mu$g/ml ampicillin) and counting surviving colonies. For the library insert generated from OL-2, a 4:1 insert:vector molar ration in the ligation gave a transformation efficiency of $3.98 \times 10^7$ transformants per $\mu$g vector DNA used in the ligation, with a large scale transformation efficiency of $4.8 \times 10^7$ transformants per ug vector. The vector alone ligation generated 40 fold fewer transformants. 10 colonies from the transformation with the OL-1 insert ligation were picked, cultured and the DNA prepared and sequenced to identify the correct clone.

The remainder of the OL-2 library SOC/transformation mixture was inoculated into 500 $\mu$l LB-amp (100 $\mu$g/ml ampicillin) and incubated at 37° C. with shaking (300 rpm). The $Abs_{600}$ of the library culture was monitored. When the culture reached an $Abs_{600}$ of 0.8 (approximately five hours), 100 $\mu$l were removed, pelleted, resuspended in 10 ml LB/15% glycerol and stored in 1 ml aliquots at −80° C. (An $Abs_{600}$ of 0.8 equals a cell concentration of approximately $10^9$ cells per ml. Therefore, for a library of $4.8 \times 10^7$, each frozen aliquot will contain 200 library equivalents).

Analysis of library diversity

Surviving colonies plated above were screened by PCR with primers flanking the degenerate region to determine the fraction of clones which contained insert (>90%). 8 insert-containing clones were picked and the nucleotide sequences of the degenerate and flanking non-degenerate regions determined. Each nucleotide was represented in the N positions with approximately 25% frequency, while G or T (but not A or C) was represented in the K positions with approximately 50% frequency. The frequency of stop codons generated in the degenerate region can be determined by this method as well.

Generation of library retrovirus and infection of Jurkat cells

DAY 0: Preparation of Phoenix Retrovirus Producer cells for Transfection:

18–24 hours prior to transfection, Phoenix cells were evenly plated at 1.5–2 million cells per 60 mm plate in Producer cell growth media (DMEM: 10% FCS, 1% Penicillin-Streptomycin, 1% Glutamine). Cells were allowed to attach for 20 hours on the plates.

DAY 1: Transient transfection: The highest transfection frequencies are obtained with Phoenix cells that are 70–80% confluent at the time of transfection. The DNA in HBS (2×HBS=8.0 g NaCl, 6.5 g HEPES, 10 ml $Na_2HPO_4$ stock (5.25 g dibasic in 500 ml water), adjusted to pH 7, to a final volume of 500 mls, with a final pH adjustment to 7) was prepared for application to the Phoenix cells. About 5 minutes prior to transfection, chloroquine (Sigma) was added to each plate to 25 uM (chloroquine stock is 50 mM in ddH2O; for 3 mL media+1 ml DNA, add 2$\mu$l). To a 15 ml conical tube, the following were added (per 6 cm plate, 5 plates total, with all reagents at room temperature):

5 ug library DNA (DNA was added in a drop to side of tube)

1 ug pMSCVpc lacZ virus vector 438 u1 dd H2O (the DNA was washed to the bottom of tube with water).

61 ul 2M $CaCl_2$ (Mallinkrodt, catalog # 4160; make up in water, sterile filter and store tightly capped at 4° C.

500 ul Total volume.

Samples were mixed thoroughly with finger tapping. Transfections with 5 ug pMSCVpc lac Z and with the OL-1 vector DNA were carried out for use as negative and positive controls, respectively.0.5 mL 2×HBS was added to each tube quickly; the solution was bubbled vigorously with the automatic pipettor by keeping the eject button depressed) for 10 sec (the actual length of bubbling time depends on each batch of 2×HBS). The HBS/DNA solution was dispersed dropwise and evenly onto the media in each Phoenix cell plate dropwise (gently and quickly). The plates were observed under a microscope; evenly distributed very small black particles of precipitated DNA (like pepper) were visible. The plates were placed in a 37 oC incubator and rocked forward and backward a few times to evenly distribute the DNA/CaPO4 particles. 6–8 hours post-transfection, the media was changed to 3 ml fresh DMEM, 10% FCS. Prior to the media change, the DNA precipitate was larger and more clearly visible under the microscope.

DAY 2: Second media change.

24 hours post-transfection, the media was changed again to 3 ml fresh DMEM, 10% FCS. The cells were placed at 32° C. (the virus is more stable if incubation is carried out at 32° C., although 37° C. is fine).

DAY 3: Transduction of Jurkat EcoR cells.

A sterile Acrodisc 0.45 micron syringe filter (Gelman Sciences) was attached to the end of a 10 ml sterile syringe and the injection stopper sterilly removed from the syringe barrel. At 48 hours post-transfection, the virus supernatant was removed from the Phoenix cells and added to the syringe barrel. The stopper was replaced and the virus supernatant was ejected dropwise into a clean, sterile conical tube. The Phoenix cell plates were set aside for X-Gal staining (see below). Polybrene was added to each viral supernatant (Sigma; 2.5 mg/ml in ddH20=500×; store at −20 oC) to a final concentration of 5 mg/ml. $4.5 \times 10^6$ Jurkat EcoR cells (Jurkat cells stably expressing the ecotropic retrovirus receptor) were pelleted for 1400 rpm for five min and resuspended in 9 mls of the OL-2 library virus supernatant. The cells were distributed in aliquots of 1 ml, or $5 \times 10^5$ cells, into the wells of a 24 well plate. $1.5 \times 10^6$ Jurkat EcoR cells were similarly treated with 3 mls each of the lacZ viral supernatant and the OL-1 viral supernatant. Each cell plate was wrapped in parafilm, placed in a microplate carrier (DuPont) and centrifuged at 2500 rpm for 90 min at 32° C. in a DuPont/Sorvall RT 6000B table top centrifuge. After centrifugation, the cells were observed under a microscope. The presence of large irregularly-shaped bodies representing fused Jurkats (each as large as 5–10 unfused cells) suggested successful infection. The parafilm was removed from the plates, which were placed at 32° C. After an additional 16 hours at 32° C., the cells were loosened from the bottom of each well with gentle trituration and added to a 15 ml conical tube. The tubes were centrifuged at 1400 rpm for five min to the pellet the cells. The cells were resuspended in 5 mls fresh RPMI,10% FCS for every three wells of cells and added to a 60 mm plate (3 wells of cells per plate). 1 ml fresh RPMI, 10% FCS was added to each well of cells remaining in the 24 well plates. Plates were kept at 37° C. for 72 hours, at which time the cells transduced with each virus were combined and an aliquot Jurkat cells stained with X-Gal. Unused viral supernatant was stored at −80° C. for future transduction, although the titer drops by one-half for each freeze-thaw cycle.

Determination of transfection efficiency

Both tranfected Phoenix cells and transduced Jurkat cells were stained with X-Gal to gauge the transfection and transduction efficiencies. The purpose of co-transfecting the pMSCVpc lacZ virus vector with the library virus vector, as described above, was to permit an indirect assessment of the efficiencies of transfection and transduction. Preparation of solutions: fixative: PBS/0.10% Glutaraldehyde. Glutaraldehyde stock (Sigma cat # G5882) is a 25% solution, or 250×; stock staining solutions: i) 300 mM/25×ferrocyanate solution: 25.3 g K4Fe(CN)6.3H2O (Mallinckrodt)+2.48 g MgCl2 (Sigma) in 200 ml H20; store at 4° C.; ii. 300 mM/25×ferricyanate solution: 19.75 g K3Fe(CN)6 (Sigma)+2.48 g MgCl2 in 200 ml H20; store at 4°; iii. XGal (Molecular Probes) is made up as a 40 mg/ml solution in DMF; store at −20° C. in the dark; iv. 1×ferro/ferricyanate solution: add 4 ml 300 mM/25×ferrocyanate solution and 4 ml 300 mM/25×ferricyanate solution to 196 ml PBS; store at 4° C. for up to one month; v. active staining solution: each time cells are to be stained, 100 µl 40 mg/ml X-Gal is added to each 3 ml 1×ferro/ferricyanate solution; washing solution: PBS for Phoenix and other adherent cells; 1% FCS in PBS for Jurkat and other nonadherent cells.

The media was removed from the 60 mm plates of Phoenix cells or $5 \times 10^5$ Jurkat cells were pelleted in a 15 ml conical tube at 1400 rpm for five min. 2 ml of fixative were added to each 60 mm plate of Phoenix cells or Jurkat cells were resuspended in 1 ml fixative. Cells were left in fixative for 2 min. For Phoenix cells, fixative was poured off and the cells were washed three times with PBS (first two washes were quick; for third wash, the PBS was left on the cells for 3 min). For Jurkat cells, the fixative was quenched by adding 5–10 ml PBS/1% FCS to each conical tube, inverting each tube five times and pelleting as before.3 ml of active staining solution were layered onto each 60 mm plate of Phoenix cells or each cell pellet of $5 \times 10^5$ Jurkat cells was resuspended in 1 ml of active staining solution and placed in a well of a 24 well plate. All cells were incubated at 37° C. The cells were observed under a microscope 24 hours later. The efficiency of transfection of the Phoenix cells was estimated as the percentage of blue cells in a field. The efficiency of transduction of the Jurkat cells was estimated by counting blue cells in a hemocytometer. Transfection with 5 µg lacZ vector produced 50% blue Phoenix cells. Transduction of Jurkats with the resulting virus produced 30% blue Jurkat cells. Co-transfection of 1 µg lacZ virus vector with 5 µg library virus vector produced 5–10% blue Phoenix cells. Transduction of Jurkats with the resulting virus resulted in 3–10% blue Jurkat cells.

Selection of Jurkat cells with lgM Anti-Fas

Titer lgM anti-Fas: A fresh batch of CH-11 lgM antibody to human Fas (Kamiya Biomedical Company; cat # MC-060)was tested to determine the effectiveness of induction of apoptosis. $5 \times 10^5$ Jurkat EcoR cells were pelleted at 1500 rpm for five min and resuspended in 1 ml RPMI/2.5% FCS plus serial dilutions of CH-11 antibody, 50 ng/ml, 10 ng/ml, 2.0 ng/ml and 0.5 ng/ml final concentration. Cells in each dilution of antibody were placed in a well of a 24 well plate at 37° C. for 48 hours, at which time 4 ml acridine orange/ethidium bromide (Sigma; 100 µg/ml each in PBS; store in the dark at 4° C.) was added to 100 ml cells on ice. Cells were examined in a hemocytometer under a 20×objective with a filter combination suitable for reading fluorescein.

2. 100 cells from each sample were counted and the number of cells in the following groups was recorded:

1. live cells with normal nuclei (bright green chromatin with organized structure).

2. early apoptotic (EA; bright green chromatin that is highly condensed or fragmented).

3. late apoptotic (LA; bright orange chromatin that is highly condensed or fragmented).

4. necrotic cells (N; bright orange chromatin with organized structure).

% apoptotic cells was calculated as EA+LA/total number of cells counted×100

Using 10 ng/ml of the CH-11 antibody, >95% apoptosis of Jurkat EcoR cells was demonstrated.

IgM Anti-Fas Selection of Library-Expressing Jurkats $9.6 \times 10^6$ OL-2 library-transduced Jurkat cells were pelleted and resuspended in 96 ml RPMI/2.5% FCS+10 ng/ml CH-11 antibody. Cells were distributed in 1 ml aliquots of $1 \times 10^5$ cells into each well of four 24 well plates. $4.8 \times 10^8$ lacZ-transduced Jurkats and OL-1-transduced Jurkats were similarly treated and each distributed into the wells of two 24 well plates. Plates were placed at 37° C. for five days. The plates were checked daily for bacterial or yeast contamination. Cells were removed from any contaminated wells and 2 ml 10N NaOH was added to the empty wells to reduce the risk of spread of contamination to other wells. Little to no live cells were observed under the microscope after 2–3 days, confirmed by the red color of the media which had not been depleted of any nutrients. Five days after initial lgM anti-Fas treatment, 1 ml RPMI/20% FCS was added to each well. The cells were left at 37° C. for an additional 10–14 days. The plates were checked frequently for contamination and treated as above. 10 days after addition of the RPMI/20% FCS, nearly every well of the OL-1-transduced cells contained live colonies of cells, confirmed by the orange color of the nutrient-depleted media. The media in all wells of lacZ-transduced cells remained red, and little cell growth was observed in any of the wells. Selected wells of the OL-2 library-transduced cells contained live cells and nutrient-depleted media. During the next two weeks, cells were removed from all wells in which significant cell growth was occurring, as guaged by observing the cells directly under the microscope and monitoring the increasing nutrient depletion of the cell media. Cells from each well were resuspended in 5 ml fresh RPMI/10% FCS and placed in a 60 mm dish at 37 oC for 2–3 days.

RNA isolation

RNA was isolated from the each surviving well population of OL-2 library-transduced Jurkat cells (17 wells), as well from five surviving well populations of OL-1-transduced cells, using the mRNA Capture Kit according to the manufacturer's protocol (Boehringer-Mannheim cat #1 787 896). Briefly: $5 \times 10^5$ cells from each dish were pelleted at 1400 rpm for five min in an Eppendorf tube, washed twice with PBS and resuspended in 200 ml lysis buffer and sheared by passing six times through a 21 guage needle attached to a 1 ml syringe. 4 ml 1:20 dilution of biotinylated oligo(dT) 20 was added to each sample and incubated for 3 min at 37° C. The mix was removed from each tube. Each tube was washed three times with 200 ml of washing buffer. Cells were also stored in 90%FCS/10%DMSO in 1 ml aliquots of 1×106 cells each in liquid nitrogen.

RT PCR rescue of peptide-encoding inserts from selected cells

PCR was carried out using the TitanTM RT-PCR System (Boehringer Mannheim cat #1 855 476), using two primers: 5'pBL primer has the sequence: 5'-GAT CCT CCC TTT ATC CAG-3' (SEQ ID NO:64) and is complementary to nucleotides 1364–1381 of all pMSCVpc-based vectors and retrovirus mRNA, just upstream of the cloned insert. 3A primer has the sequence 5'-CTA CAG GTG GGG TCT TTC-3' (SEQ ID NO:65) and is complementary to a sequence in all pMSCVpc-based vectors and retrovirus mRNA, just downstream of the cloned insert.

Re-cloning rescued peptide-encoding inserts

Each PCR-rescued sample was extracted with phenol chloroform, ethanol precipitated and resupsended in 25 ml 10 mM Tris pH 8.5. 3 ml nondenaturing DNA gel loading dye was added to 10 ml of each sample and run on a 10% acrylamide minigel with oligonucleotide quantitation standards and a 10 base pair ladder, as described above. Each lane contained one prominent band with the expected molecular weight of 216 base pairs and minor background bands. The molarity of each sample was quantitated using NIH Image as before. Each sample was BstXI restriction digested, phenol extracted, ethanol precipitated and resuspended in 25 ml 10 mM tris pH 8.5. The purified samples were loaded onto 10% acrylamide gels and quantitated as before. All samples contained a prominent band of 55 base pairs, the expected molecular weight for the restriction digested insert, as well as bands of 100 base pairs and 51 base pairs corresponding to each of the ends of the rescued DNA insert removed by the restriction enzyme. Each restriction digested, PCR-rescued insert was ligated at a 4:1 insert:vector molar ratio with 100 ng pMSCVpc vector DNA, precipitated and electrotransformed as before. Surviving colonies for each transformation were PCR screened using the 5'pBL and 3A primers. 8 to 10 insert-containing colonies for each transformation were cultured overnight, the cultures were pooled and a single mini-DNA preparation carried out for each pool. Fas-Selected Peptide clones: All peptides have the sequence: MET GLY LYS ARG LYS GLY XXX XXX XXX D/E XXX VAL GLY PRO PRO (SEQ ID NO:62). Only the xxx xxx xxx D/E xxx amino acids are written above each DNA sequence below.

From first library selection well:

```
From first library selection well:
L1B3 INDIVIDUAL CLONES, FAS-SELECTED.

TSR ALA SER ASP ALA  (SEQ ID NO:67)
L1B3E1 ATG GGC AAG AGA AAG GGC ACG GCG TCT GAT GCT  (SEQ ID NO:66)
GTG GGG CCC CCT TAA

TYR PRO SER ASP VAL  (SEQ ID NO:69)
L1B3E2 ATG GGC AAG AGA AAG GGC TAT CCT TCT GAT GTG  (SEQ ID NO:68)
GTC GGG CCC CCT TAA

THR PRO SER ASP MET  (SEQ ID NO:71)
L1B3E3 ATG GGC AAG AGA AAG GGC ACG CCT TCG GAT ATG  (SEQ ID NO:70)
GTC GGC CCC CCT TAA

THR ALA SER ASP LEU  (SEQ ID NO:73)
L1B3E6 ATG GGC AAG AGA AAG GGC ACG GCT TCT GAT CTT  (SEQ ID NO:72)
GTG GGG CCC CCT TAA

SER ASP ARG ASP ILE  (SEQ ID NO:75)
L1B3E7 ATG GGC AAG AGA AAG GGC TCT GAT AGG GAT ATT  (SEQ ID NO:74)
GTG GGG CCC CCT TAA

From second library selection well:
L2A5 INDIVIDUAL CLONES, FAS SELECTED.

TRP LEU LEU GLU PHE  (SEQ ID NO:77)
L2A5A2 ATG GGC AAG AGA AAG GGC TGG TTG CTA GAG TTT  (SEQ ID NO:76)
GTG GGC CCC CCT TAA

TRP LEU ILE GLU PHE  (SEQ ID NO:79)
```

```
                                    -continued
L2A5A3 ATG GGC AAG AGA AAG GGC TGG TTG ATA GAG TTT    (SEQ ID NO:78)
GTG GGG CCC CCT TAA TRP LEU LEU GLU PHE     (SEQ ID NO:77)
L2A5AG ATG GGC AAG AGA AAG GGC TGG TTG CTA GAG TTT    (SEQ ID NO:76)
GTG GGG CCC CCT TAA TRP LEU LEU GLU PHE     (SEQ ID NO:77)
L2A5A8 ATG GGC AAG AGA AAG GGC TGG TTG CTA GAG TTT    (SEQ ID NO:76)
GTG GGG CCC CCT TAA SER TYR GLN ASP LEU    (SEQ ID NO:81)
L2A5A9 ATG GGC AAG AGA AAA GGC TCT TAC CAA GAT CTG   (SEQ ID NO:80)
GTG GGG CCC CCT TAA
```

Example 3

Staurosporine Selection of NIH 3T3 Cells Transduced with pBabe Puro Peptide Library A. Library construction Construction of the pBabe puro random peptide library was described earlier in the patent. The randomized peptide has the sequence: MGXXXXXXXXXXGGPP (SEQ ID NO:82) The diversity of the library is $2 \times 10^8$ at the DNA insert level.

B. Library transfection

Transfections were carried out as described for Fas-selection, but in 15 cm plates of $10^7$ Phoenix cells. The DNA solution added to each plate consisted of: 50 ug library DNA, 5 ug lacZ vector, 4340 ul ddH$_2$O, 610 ul 2M CaCl$_2$ and 5000 ul 2×HBS.

C. Library transduction 24 hours prior to transduction, $2 \times 10^7$ NIH 3T3 cells were plated in each of ten 15 cm plates in 25 ml DMEM, 10% Bovine Calf Serum. 5 ml library virus supernatant was added to each plate (plus polybrene as before). 24 hour after transduction, media was changed to 25 ml fresh DMEM, 10% BCS. Cells were stained with X-gal at 48 hours post-transduction. The transduction efficiency was estimated as 40–50%.

D. Staurosporine selection

Staurosporine, an alkaloid from Streptomyces sp., is a potent, broad spectrum inhibitor of protein kinases which binds the ATP site. Addition of 1 uM staurosporine in serum-free media to NIH 3T3 cells induced >99% apoptosis within 24 hours, as determined by ethidium bromide/acridine orange double staining as described for the Fas selection.

$2 \times 10^6$ library-transduced NIH 3T3 cells were plated in each of 10 15 cm plates. Cells wer allowed to attach for 24 hours, at which time staursporine was added to 1 uM in serum free DMEM. LacZ-transduced NIH 3T3 cells and BCL-2-transduced NIH 3T3 cells were used as negative and positive controls, respectively. 24 hours after stuarosporine treatment, the media was changed to 25 ml fresh DMEM, 10% BCS. The media was changed every two days for one week, until the sruviving cells looked healthy (typical 3T3 morphology), at which time 1 uM staurosporine in serum-free media was added again. The media wash changed to DMEM, 10% BCS as before. Stp treatment was carried out again for a total of three treatments, at which time the number of library-transduced cells suriving appeared greater than the number of lacZ-transduced cells (but less than the BCL-2-transduced cells.

E. Moloney transfer

After the second staurosporine treatment, aliquots of surviving cells from each plate were infected with wild type Moloney murine leukemia virus supernatant. (generated by transfecting Phoenix cells with the retroviral vector pZap). The virus was allowed to spread through the culture for one week (with re-plating of the cells every 2–3 days). Cells were plated as before and treated with Staurosporine before proceeding to RNA isolation and PCR rescue.

F. RNA isolation

Aliquots of cells surviving in each plate were resuspended in 90% FCS, 10% DMSO and stored in liquid nitrogen. RNA was prepared with Trizol reagent (Gibco BRL, cat # 15596-026). Briefly, 1 ml TRIzol reagent was added were 10 cm$^2$ monolayer of cells and incubated for 5 min at room temperature. Cell lysates were transferred to 15 ml conical tubes. (Note: at this point, DEPC-treated solutions and glassware were used exclusively). O.2 ml chloroform was added per 1 ml TRIzol reagent used. Tubes were shaken for 15 sec, incubated for 3 min at room temperature and centrifuged at 12000×g for 15 min at 4° C. The RNA-containing upper aqueuous phase was removed and 0.5 ml isopropanol added per 1 ml TRIzol used for the initial homogenization. Samples were mixed and incubated at room temperature for 10 min followed by centrifugation as before. the supernatant was removed and the RNA pellet washed with 75% ethanol (1 ml per 1 ml TRIzol). The sample was vortexed and centrifuged at 7500×g for 5 min at 4° C. The RNA pellet was air-dried for 10 min and resuspended in RNase-free water with 10 min incubation at 60° C. to dissolve the pellet. RNA concentration was determined by measuring the absorbance at 260 nm.

G. PCR rescue

PCR rescue was carried out as for Fas selection, using the primers 5'pBL and SV 40 down. The second primer has the sequence: 5' CTG ACA CAC ATT CCA CAG 3' (SEQ ID NO:83) and is complimentary to positions 1424–1441 of the pBabe Puro retroviral vector. PCR reactions were extracted with phenol-chloroform, precipitated with ethanol and digested with Bam HI and Sal I before ligation with the retroviral vector pWZL neo. The figure shows a 10% acrylamide gel of representative PCR-generated inserts:

Lane 1: 10 base pair ladder

Lane 2: undigested PCR insert from Stuarosporine-selected cell population

Lane 3: undigested PCR insert from same cell population, after Moloney rescue and Staurosporine selection.

Lanes 4 and 5: same as lanes 2 and 3, after restriction digestion.

H. Secondary screen pWZL neo vectors containing rescued inserts were transfected into Phoenix cells, and the resulting virus used to transduce NIH 3T3 cells. Staurosporine selection was repeated three times as before, before RNA preparation and PCR rescue.

I. Sequences of the first 9 positives

The sequences of the first nine positives are as follows:

```
SEQUENCE OF 2 P 1

GGATCCAGTGTGGTGGTACGTAGGAATACC-                                (SEQ ID NO:84)
ATG GGA TGT CGG TCT GTT GCT AGG CCG CGG GGT GGT GGG GGC CCC CCC
Met Gly Cys Pro Ser Val Ala Arg Pro Arg Gly Gly Gly Gly Pro Pro (SEQ ID NO:85)
TAGCTAACTAAAGATCCCAGTGTGGTGGTACGTAGGAATTCGCC 2P1
Stp Stp Stp Bam /Bg

SEQUENCE OF 4 P 1

GGATCCCAGTGTGGTGGTACGTAGGAATACC-                               (SEQ ID NO:86)
ATG GGA TTG TCT TTT GTT ATT (C/TGT GTG CAG CAT CGT GGG GGC CCC
Met Gly Leu Ser Phe Val Ile Arg Leu Gln His Arg Gly Gly Pro    (SEQ ID NO:87)
CCC TAG CTAACTAAAGATCCCAGTGTGGTGGTACGT 4P1
Pro Stp Stp StpBam /Bg
    Cys

SEQUENCE OF 5 P 1

GGATCCGAGTGTGGTGGTACGTAGGAGTACC-                               (SEQ ID NO:88)
ATG GGA GCT CCG ATT TGG TAT ACT CAT TGG AGT CAT GGG GGC CCC CCC
Met Gly Pro Pro Ile Trp Tyr Thr His Trp Ser His Gly Gly Pro Pro (SEQ ID NO:89)
TAG CTAACTAAAGAT CG 5P1
Stp Stp StpBam /Bg

SEQUENCE OF 6 P 1

GGATCCCAGTGTGGTGGTACGTAGGAGTACC-                               (SEQ ID NO:90)
ATG GAA GTC AGG CGT TTG TGA ATA CTC GGC ATA AG GGC CCC GGG CCC
Met Glu Val Arg Arg Leu Stp                                    (SEQ ID NO:91)
Gly Gly Pro Pro                                                (SEQ ID NO:3)
TAGCTAACTAAAGAT CC 6P1
Stp Stp StpBam /Bg

SEQUENCE OF 7 P 1

CCGGCCGTATTCAACAAGGGGCTGAAGGATGCCCAGAAGGTACCCCATTGTATGGGATCTGAT (SEQ ID NO:92)
CTGGGGCCTCGGTGCACATGCTTTACATGTGTTTAGTCGAGGTTAAAAAACGTCTAGGCCCCC
7P1

SEQUENCE OF 8 P 1

GGATCCCAGTGTGGTGGTACGTAGGAATACC                                (SEQ ID NO:93)
ATG GGA CTT TAG CCG GGC CCC CCC TAGCTAACTAAAGATCCCAGTGTGGTGGT
Met Gly Leu Stp       Pro Pro Stp Stp Stp Bam /Bg
ACGTAGGAATTCGCCAGCACAG T 8P1

SEQUENCE OF 9 P 1

GGATCCCAGTGTGGTGGTACGTAGGAATACATG                              (SEQ ID NO:94)
GGA ACT GTT ATG GCG ATG TCG GAT TAG GTC GAG    GGG GGC CCC CCC
Met Gly Thr Val Met Ala Met Ser Asp Stp                        (SEQ ID NO:95)
Gly Gly Pro Pro                                                (SEQ ID NO:3)
TAGCTAAGTAAAGATCC 9P1
Stp Stp Stp Bam /Bg

SEQUENCE OF 10 P 1

GGATCCAGTGTGGTGGTACGTAGGAATACC                                 (SEQ ID NO:96)
ATG GGA TGT CCG TCT GTT GCT AGG CCG CGG GGT GGT GGG GGC CCC CCC
Met Gly Cys Pro Ser Val Ala Arg Pro Arg Gly Gly Gly Gly Pro Pro (SEQ ID NO:97)
TAGCTAACTAAAGATCC 10P1
Stp Stp Stp Bam /Bg
```

Example 4

Use of NF-κB and NFAT in Signalling

The NFκB/IkB complex is the classic pro-inflammatory second messenger system, known to be involved as a positive regulator of a number of pro-inflammatory processes and cytokines. These include, but are not limited to, IL-1, IL-6, IL-8, and TNF-α. As well, anti-inflammatory interleukins, such as IL-4, can lead to direct down-modulation of NF-kB in synovial fibroblasts and concommitant downregulation of IL-6 production. The NF-kB/IkB complex is a widespread, acute-phase, rapid-response transcriptional activation system. It operates in most cell types tested, but leads to different outcomes dependent upon the cell type and the nature of the initiating stimulus. Activators of NF-kB include LPS, TNF-α, IL-1, inducers of T cell activation, protein synthesis inhibitors, phorbol esters, and a-IgM. Other inducers include the viruses Adenovirus, HTLV I, cytomegalovirus, Sendai, and Herpes simplex I, agents that cause cellular damage such as ultraviolet light and peroxides, and phosphatase inhibitors such as okadaic acid. These inducers act through PKA and PKC-dependent pathways, double-strand RNA-dependent kinase, and other pathways. Pharmacologic regulators of NF-kB, such as salicylate and glucocorticoids, act by either preventing IkB-α degradation or lead to upregulation of IkB-a transcription and steady-state levels, thereby acting to prevent the activation of this critical factor.

NF-kB (Nuclear Factor that binds to the k locus B site) is present in the cytoplasm of most cells in an inactive form complexed to IkB (Inhibitor of NF-kB). Certain stimuli received by cells are processed by cellular signaling mechanisms and integrated in the specific phosphorylation of IkB and its degradation. The regulation of IkB-a function is through a Signal Response Element (SRE) in the amino terminus of the molecule. Phosphorylation of serine residues 32 and 36 leads to recognition of the IkB-a molecule by the ubiquitination machinery, release of NF-kB to the nucleus, and degradation of IkB. Therefore, dependent upon the phosphorylation/degradative state of IkB, NF-kB is either maintained in the cytoplasm or released to the nucleus. In the nucleus NF-kB binds to a consensus DNA motif found near the regulatory regions of many characterized genes and therein acts as a transcriptional regulator. Importantly, from the point of view of infectious disease, NF-kB is a primary activator of the Human Immunodeficiency Virus (HIV). Suitable induced genes include TNF-α and IL-6.

Biochemically, NF-kB is defined as a heterodimer of two polypeptides, p50 and p65, of corresponding molecular mass 50 and 65 kD, respectively. p50 is processed from a 105 kD precursor protein by an as yet uncharacterized mechanism. p65 is the receptor for IkB and is the molecule through which IkB exerts its inhibitory/regulatory effects on NF-kB. These are the prototypic trasncription factors that define a large family of classical Rel/NF-kB factors.

Cloning of the p50 and p65 components of NF-kB led to the discovery of a family of related factors, termed Rel. Both p50 and p65 have a 300 amino motif (Rel) at their amino termini that was originally described in the proto-oncogene c-rel and the Drosophila axis-determining gene, Dorsal. The family of polypeptides revealed by p50 and p65 have overlapping DNA-binding specificities, differential tissue distribution, and complex regulatory phenomena. p105(p50) is representative of the ankyrin-motif-containing Rel proteins that are processed in the cytoplasm to smaller proteins lacking the carboxyl terminus. The carboxyl terminus of p105 shows structural and functional homologies to IkB (which also has ankyrin motifs) and functions with an IkB-like activity both in cis and in trans. p65 is representative of a second group of Rel proteins that have divergent carboxyl termini—these regions have been suggested to encode transcriptional activation domains. The 300 amino acids of Rel domains manifest four important functions: 1) DNA-binding in the roughly amino-terminal ⅓ of the domain, 2) dimerization in the carboxyl portion of the domain, 3) interaction with ankyrin-containing IkB-like proteins, and 4) nuclear-localizing signal at the carboxyl terminus of the Rel domain. In p50 the Rel domain also includes a transcriptional activation domain.

NFAT, the Nuclear Factor of Activated T Cells (NFAT), is the immediate early acute phase response factor for T cell activation. Inhibition of NFAT by cyclosporin A (CsA) leads to blockade of IL-2 production and loss of T cell commitment to activation. NFAT, a critical component of pro-inflammatory events carried out by T cells, is also the factor blocked by CsA in transplantion. Upon cloning NFAT it was clear contains a region of the molecule implicated in DNA binding that has significant homology to the Rel family of proteins. Based on structural considerations, homology comparisons, and similar modes of action, as well as genomic structures of the molecules idiccate similar intron/exon boundaries in NF-kB and NFAT families, thus indicating that NFAT actually belongs to the Rel family of factors by lineal descent and that its interaction with pro-inflammatory trasncriptional regulators of the bZIP family would follow a general set of rules common to the NF-kB/bZIP interactions.

We have shown that NFAT is involved in pro-inflammatory response to mitogens in activation of HIV-1 (S. Kinoshita and G.P.N, submitted) and that the binding of NFAT to sites overlapping the NF-kB sites of HIV-1 is reponsible for this process. This work follows on work by others showing that NFAT can regulate TNF-a activation in interaction with ATF-2/Jun and GM-CSF. Interestingly, NFAT also appears to be involved in regulation of mast cell release of IL-4, an important regulator of pro-inflammatory cytokines, such as IL-1β, TNF-α and IL-6. The activity of NFAT in these systems has all shown to be pharmacologically modulated by CsA. Thus, although NFAT was originally discovered as a T cell specific factor, it was later found to be responsible for a host of immediate early, acute phase response activities, as well as direct regulation of IL-4.

Therefore, the extended Rel families of NF-kB and NFAT make attractive targets for inhibition and modulation of pro-inflammatory action. Their involvement in numerous regulatory pathways and their decisive roles in such processes, including the specific interactions they elaborate with bZIP proteins, make them attractive specific targets for inhibition.

Reporter Genes for Detection of TNF-α and IL-1 Promoter Activity

We designed a retrovirus-based luciferase reporter-gene system driven by a minimal promoter and two lgk NF-kB sites. In the constructs presented here, the deletions I introduced were more extensive than those previously published, since preliminary experiments showed that residual enhancer activity resided in commonly available deletion constructs (Nolan, Saksela and Baltimore, unpublished). The vectors designed were pSinll-luc (containing a luciferase gene in the retroviral sense orientation to test for residual promoter activity in the construct backbone), pSinll-fosluc (identical to pSinll luc except contains a minimal fos promoter element to test for residual enhancer activity in construct backbone), and pSinll-2 kBfosluc (derived from pSinll-fosluc with 2 lgk kB sites cloned 5' proximal to the fos minimal promoter as a reporter for NF-kB activity). These three vectors used to infect $1\times10^6$ 70Z/3 cells. 70Z/3 is a murine pre B cell line originally used in the initial characterization of NF-kB. After 48 hours, the infected cells were split into two fractions (stimulated with LPS and unstimulated). Six hours later, cell extracts were prepared and assayed for luciferase activity (extract representing $\sim10^4$ cells was used for each point). The results showed that Sinll-luc showed no indiction, Sinll-fosluc showed roughly a one-fold increase, and Sinll-2 kBfosluc showed a four fold induction in lucerifase activity. Accordingly, retrovirally based reporter constructs can be used to sensitively report NF-kB activity in native chromatin. It now becomes possible to combine reporter gene technology with retroviral delivery of effector peptides. Unstimulated cells and stimulated controls (uninfected and Sinll-luc) showed little or no activity. Importantly, then, retroviral delivery did not result in significant background induction of NF-kB activity, a problem with other transfection procedures. The SinlI-luc and pSinlI-fosluc controls shows no significant residual promoter or enhancer activity in the construct. No significant readthrough from endogenous genomic loci or endogenous enhancer activity that might obscure readings was detected. These latter results are consistent with previous work using gene search retroviruses employing lacZ and flow cytometry. In these studies less than 0.1% of random integration events showed endogenous cis-regulation of the integrated constructs.

These construct designs will be used as the basis for rapid creation and testing of TNF-α and IL-1 promoter studies in T cells, macrophages, and synovial cells. We will incorporate in the place of luciferase either the lacZ or GFP cDNAs for FACS-based assay. We will place up to three to four kilobases of TNF-α or IL-1 promoter region in place of the minimal promoter employed here. These constructs will be used as a proxy measure of endogenous TNF-α and IL-1 promoter activity and will serve to allow for searches for peptides from our libraries that act upon NF-kB or NFAT as well as unknown signaling pathways that are independent of NF-kB or NFAT critical to TNF-α and IL-1 signaling.

The B cell lines to be used are 70Z/3. T cells to be used are human Jurkat. Macrophage lines to be used are Raw 309 and the P388D1 line which is highly responsive to PMA induction of secreted IL-1. Synovial cells to be used are HIG-82 and can be activated with IL-1 to induce metalloproteases and with TNF-α to induce NF-kB. IL-1 induction of metalloproteases acts through NF-kB on collagenase and other metalloproteases of this group. Thus, we have shown that β-gal fused to IkB-α and delivered via a retrovirus to cells responds to stimuli that degrade IkB-α as follows: a) 70Z/3 pre-B cells were infected with a retrovirus expressing a fusion of β-gal to either wild-type IkB-α or an inactive, dominant negative IkB-α; infection efficiency was approximately 30%. Cells were stimulated with LPS for varying times and then loaded with FDG for measure of b-gal expression by FACS. b) Cells from (a) were induced for maximal LPS induction of IkB-a degradation and treated with either salicylate or control. Salicylate blocked degradation of the β-gal-IkB fusion to the same extent as the dominant negative IkB-α.

Direct detection in living cells of steady state levels of IkB-α

At the first approach, NF-kB activation will be measured using our newly developed IkB-α mobile reporter system described above. In this approach, the N-terminus of IkB-α has been translationally fused to the lacZ gene. In mammalian cells, β-galactosidase expression can be measured using the Fluorescence activated Cell Sorter (FACS) on a cell by cell basis. By coupling β-gal to IkB-α, the stability of β-gal is functionally dependent upon IkB-α. Since signals in cells that activate NF-kB lead to the degradation of IkB, β-gal was similarly degraded; as above, cells were infected with a retrovirus containing a β-gal-IkB-α fusion and induced them with stimuli that lead to activation of NF-kB. We can use the cell sorter to distinguish cells that have degraded IkB-α on a REAL-TIME basis, and not through activation of proxy reporter genes. These lines were shown to respond accordingly after treatment with the anti-inflammatory agent salicylate (aspirin) which has been shown to be a direct inhibitor of NF-kB activation. We have used this and related protocols in B cells to select for novel mutants of IkB-α and have thereby defined new regions of the IkB-α molecule that respond to differential signaling (J. Caldwell and G. Nolan, unpublished).

$1 \times 10^7$ cells carrying the reporter will be infected at high efficiency with the molecular libraries described herein. Cells will be stimulated with LPS, TNF-α, IL-1 or PMA, and then used to select by FACS for those cells that DO NOT degrade β-gal. After growing out of the cells, the population will be restimulated as before and sorted again. Cells will be sorted until the population is 100% heritable for the lack of degradation phenotype. Inserts will be rescued, recloned into a retrovirus construct, and then screened again until a trans-phenotype can be confirmed. Peptides will be sequenced as noted.

Selection NFAT-deficiency using cell-death induction by NFAT dependent pathways

We have devised a system for selecting for blockade of NFAT signaling in cells that can be employed with our retroviral libraries. The system is based upon findings by Serafini and colleagues in which they were able to create a cell line whose death was dependent upon activation of NFAT. Cells stimulated by activators of T cells or NFAT lead to activation of NFAT and its translocation into the nucleus. Activation leads to induction of the diptheria toxin A gene such that the cells undergo rapid cell death. This is shown using Propidium iodide as a measure of cell viability. Thus, in a large population, those cells that are blocked for NFAT activation by peptides that interfere with the signaling system will survive. Serafini and colleagues used the approach to select for mutants in T cells signaling. We will use this proven NFAT-dipA systemin our peptide selections.

Again, cells will be infected as above with appropriate peptide libraries and screened for blockade of NFAT signaling. This basic approach, if successful, might be similarly applied to TNF-α or IL-1 signaling.

There is expectation that signaling systems exist whose purpose is to provide either pro-inflammatory and anti-inflammatory signaling. As noted above, IL-4 for instance can blockade IL-6 signaling in cells. Induction of glucocorticoid expression leads to upregulation of IkB and thereby blocks NF-kB activation. Activation of anti-oxidant pathways is well known to be similarly anti-inflammatory. Salicylate blocks NF-kB through regulation of cellular oxygenase levels. Although the peptide searches outlined above might find players in such pathways intracellularly, we desire to search for surface molecules that might initiate such protective cascades.

The peptide libraries in constructs for secreted peptides and tethered peptides will be used in T cell, macrophage, and B cell systems to select for blockade OR activation of NF-kB induction. Stimuli will include TNF-α and IL-1 for blockade. Activation will utilize the FACS-based systems in"reverse". That is, we will look for peptides whose expression leads to constitutive activation of and NF-kB reporter construct. In this case the reporter construct can be a TNF-a reporter driving lacZ or GFP. The construct can similarly be IL-1 driving lacZ or GFP. For endogenous loci, we can select for cells that induce VCAM or ICAM-1 expression after IL-1 signaling by FACS, both known to be pro-inflammatory responders. Again, both positive AND negative selection can be employed. For cells expressing tethered peptides, the selection is straightforward as the intracellular peptides above. Post-definition of the peptide sequence, it will be necessary to synthesize the peptide without the tether synthetically and determine if the peptide can workin the absence of the tether.

For secreted peptides the setup is more difficult, as the responder cell must display the phenotype and we must trace the peptide back to the SECRETING cell. For this approach we can use any reporter gene or endogenous gene in the target cells as the readout. The cells to be infected and which will secrete the peptides will be NIH3T3. $1 \times 10^7$ 3T3 cells will be infected with a fully representative library as outlined above. Cells post-infection will be allowed to form colonies of up to 10–20 cells. At this point media will be removed and the cells will be overlayed with a thin layer of 0.25% agar in media. Once solidified, a thin, porous membrane will be placed over the cells, and we will then overlay on this plate the responder cells at high density, also in 0.3% agar. Plates and membranes will be marked with indigo black. In this way secreted product can diffuse to the responder cells. For selection of PRO-inflammatory secreted peptides, after 48 hours responder cells will be lifted from the plate on the membrane and the membrane/cells/agar will be flipped onto a correspondingly sized nitro-cellulose membrane. Cells will be lysed in situ by Sarcosyl or other appropriate detergent and then applied on the membrane to a high-salt solution and suction below the nitrocellulose. In this way cellular proteins will leach out of the agar matrix and bind to the nitrocellulose. The nitrocellulose can then be treated like a "Western" for induction or blockade of any of a number of different cellular proteins. In initial tests we will use reporter genes driving enzymes such as b-gal or alkaline phosphatase to ensure assay sensitivity. As we perfect the assay it should be possible to set up direct measures of certain endogenous loci (such as TNF-α, NF-kB p65, etc.). Once cell areas on the membrane are noted, they can be traced back to the secretion cells by the indigo marking of the plates and alignment. NIH-3T3 cell "patches" corresponding to the appropriate area can be picked, expanded, and retested. As a positive control, viruses expressing TNF-α or IL-1 will be used in initial scaled mock-ups to calibrate the sensitivity of the search for pro-inflammatory peptides.

Similarly, one can search for blockade of pro-inflammatory signaling. In this case, at 24 to 36 hours post plating of the reponder cells, we will add a pro-inflammatory cytokine such as IL-1 or TNF-a to the agar layers in a liquid overlaying the agar/responders. The plate is now, from bottom to top: Secretor Cells/Membrane/Responder Cells/Liquid Overlay. The pro-inflammatory inducer will diffuse into the reposnder cells layer rapidly. Those cells that have been "protected" from pro-inflammatory events by a localized presence of an anti-inflammatory secreted peptide will not respond to the stimuli. As above, these can be detected against a background of responders by a nitrocellose assay for enzymatic activity. The latter, that is looking for "holes" against a background of positivity on the nitrocellose can be used to screen for inhibitors of pro-inflammatory events. As a positive control, viruses expressing IL-4 will be used in initial mock-ups to calibrate the sensitivity of the search for anti-inflammatory peptides.

We claim:

1. A method of screening for a transdominant bioactive agent that alters the phenotype of a cell, said method comprising time steps:
   a) introducing a molecular library of randomized candidate nucleic acids operably linked to a presentation sequence into a first plurality of cells, wherein each of said nucleic acids comprises a different nucleotide sequence, wherein said randomized candidate nucleic acids are expressed in said first cells to produce a plurality of randomized peptide; and
   b) screening said first plurality of cells for a cell exhibiting an altered phenotype, wherein said altered phenotype is an effect on a second plurality of cells which are co-cultured with said first plurality of cells, and wherein said altered phenotype is due to the presence of a transdominant bioactive agent.

2. A method according to claim 1 further comprising the step:
   c) isolating said cell exhibiting an altered phenotype.

3. A method according to claim 2 further comprising the step:
   d) isolating a candidate nucleic acid from said cell exhibiting an altered phenotype.

4. A method according to claim 2 or 3 further comprising the step:
   e) isolating a target molecule using
      i) a candidate nucleic acid; or
      ii) the expression product of a candidate nucleic acid.

5. A method according to claim 1 wherein said candidate nucleic acids are each operably linked to a nucleic acid encoding a fusion partner.

6. A method according to claim 1 wherein said presentation sequence presents said expression product in a conformationally restricted form.

7. A method according to claim 5 wherein said fusion partner comprises a targeting sequence.

8. A method according to claim 7 wherein said targeting sequence is selected from the group consisting of:
   a) a localizing signal sequence that localizes said randomized peptides to a predetermined subcellular locale;
   b) a membrane-anchoring signal sequence that localizes said randomized peptides to a cellular membrane; and
   c) a secretory signal sequence that effects the secretion of said randomized peptides.

9. A method according to claim 1 wherein said introducing is with retroviral vectors.

10. A method according to claim 1 wherein at least one plurality of said first and second plurality of cells are mammalian cells.

11. A method according to claim 1 wherein said library comprises at least $10^4$ different nucleic acids.

12. A method according to claim 1 wherein said library comprises at least $10^5$ different nucleic acids.

13. A method according to claim 1, wherein said library comprises at least $10^6$ different nucleic acids.

14. A method according to claim 1 wherein said library comprises at least $10^7$ different nucleic acids.

15. A method according to claim 1 wherein said library comprises at least $10^8$ different nucleic acids.

* * * * *